United States Patent [19]

Van Oosterhout

[11] B 4,002,823

[45] Jan. 11, 1977

[54] METHOD AND APPARATUS FOR VIDEO INSPECTION OF ARTICLES OF MANUFACTURE

[75] Inventor: Jack T. Van Oosterhout, Conklin, N.Y.

[73] Assignee: Ball Corporation, Muncie, Ind.

[22] Filed: Nov. 1, 1974

[21] Appl. No.: 520,227

[44] Published under the second Trial Voluntary Protest Program on March 30, 1976 as document No. B 520,227.

[52] U.S. Cl. .................. 358/106; 178/DIG. 37; 250/223 B; 356/237; 356/239; 356/240
[51] Int. Cl.² ............................. H04N 7/18
[58] Field of Search ........... 178/DIG. 37, 6.8; 356/237, 239, 240; 250/223 B

[56] References Cited

UNITED STATES PATENTS

| | | | |
|---|---|---|---|
| 2,798,605 | 7/1957 | Richards | 178/DIG. 37 |
| 3,049,588 | 8/1962 | Barnett | 178/DIG. 1 |
| 3,560,096 | 2/1971 | Watson et al. | 178/6 |
| 3,579,249 | 5/1971 | Dewey et al. | 178/DIG. 37 |
| 3,647,961 | 3/1972 | Blitchington et al. | 178/DIG. 37 |
| 3,746,784 | 7/1973 | Van Oosterhout | 178/6.8 |

Primary Examiner—Robert L. Griffin
Assistant Examiner—Edward L. Coles
Attorney, Agent, or Firm—James D. Haynes

[57] ABSTRACT

A method and apparatus for detecting defects in articles of manufacture such as glassware having lettering, mold marks and coloring is disclosed with the apparatus including a semi-diffused light source positioned adjacent one side of and optically spaced from the article being inspected for illuminating the article. A video camera is positioned on the opposite side of the article from the diffused light source and scans the illuminated article in order to produce a video signal indicative of the difference in the refraction characteristics of the article to thereby indicate the presence or absence of defects in the glassware sample. Circuitry is disclosed for discriminating between true defects and lettering, mold marks and coloring normally associated with the article. In the event there is a defect, an electrical processing circuit connected to the video camera and responsive to the video signal is provided for actuating a glassware rejection mechanism. Circuit means are also disclosed for inspecting round objects, such as the bottoms of round jars or glasses.

18 Claims, 13 Drawing Figures

METHOD AND APPARATUS FOR VIDEO INSPECTION OF ARTICLES OF MANUFACTURE

BACKGROUND OF THE INVENTION

This invention relates broadly to an assembly for detecting defects in articles of manufacture and more specifically, relates to a method and apparatus for automatically detecting defects in glassware.

It is oftentimes necessary to monitor articles of manufacture to assure that desired product quality levels are achieved. It is readily apparent, for example, to those having knowledge in the manufacture of glassware that finished glassware products may not be perfectly formed and may therefore in some cases not be entirely suitable for the use intended. By providing monitoring or inspection devices to eliminate those articles of manufacture which are not entirely suitable and therefore considered defective for a specific use, product quality can be enhanced. In glassware "spikes" which are sharp glass projections formed in glassware and "birdswings" which are found generally in bottles and which comprise thin pieces of glass extending across opposite inner walls thereof are examples of items for which glassware is often inspected and glassware rejected if present. Obviously, monitoring or inspection systems and a degree of reliability inherent in any such system for monitoring unwanted characteristics in finished glassware products or other such articles of manufacture are often important in achieving quality of the product.

Heretofore monitoring systems for detecting defects in glassware have taken various forms ranging from, for example, mere visual inspection utilized in the slow production of glassware to complex electronic detection systems utilized in the more rapid production of glassware.

As an example of an early electronic inspection device, Fedorchak disclosed in U.S. Pat. No. 2,649,500 a glass inspection apparatus wherein ultraviolet light was directed into the inside of a bottle. The ultraviolet light was reflected out of the bottle onto a mosaic which was in turn scanned by a cathode-ray tube. The cathode-ray tube scanned the mosaic in a spiral manner to thereby provide an indication when a flaw, such as a sharp projection, occurred in the bottle. This apparatus had the drawback in that a lamp had to be positioned such that light could be directed into the inside of the bottle so that the light would be reflected therefrom. This prohibited rapid assembly line inspecting of bottles. In addition, no means were taken into account for the change in reflected ultraviolet light due to the corners of the glass jar and for other normal variances in the contour of the bottle caused by, for example, seams and lettering.

A more recent development was disclosed by Gambrell et al in U.S. Pat. No. 3,379,829 wherein a fault detection apparatus was disclosed wherein normal perturbations in the glassware were not detected because a mask corresponding to the shape of the inspected article of manufacture provided blanking signals when normally encountered perturbations on the surface were scanned by an electronic beam. Such an arrangement, however, requires that the mask be appropriately aligned with the article being inspected and eliminates the possibility of checking flaws positioned between the masked portion of the article and the source of radiation which is detected.

Richards disclosed in U.S. Pat. No. 2,798,605 an electronic inspection apparatus for detecting foreign matter in bottles. In the Richards' invention, bottles are passed along a conveyor line and are passed in front of the optical system of a television camera. As each object passes in front of the camera, a light flash of short duration is provided to thereby illuminate the object and cause an image to be transmitted to the mosaic of the television camera tube. The mosaic is scanned by the cathoderay gun of the camera tube which provides an output signal that indicates appreciable discontinuity of the video signal from its average level. However, this invention requires a rather complex "herringbone" sweep action in order for the inspection apparatus to distinguish between the sides of the bottle and true defects. Further, two transverse views are required of each bottle in order to detect flaws along the vertical length of the bottle, thereby requiring two separate camera systems. Thus, while Richards was an improvement in the art, the method and apparatus required for inspecting the bottles remained quite complex.

In U.S. Pat. No. 3,746,784, issued to the inventor of the present invention and assigned to the common assignee herewith, an electronic defect detecting apparatus was disclosed which included a video camera for scanning bottles as they passed in front of the camera. Circuitry was provided for eliminating the signals caused by the leading and trailing edges of the bottles so that these signals would not be considered as defects. However, this invention was designed to inspect flint glass and could not accurately and reliably inspect all types of bottles or flasks, including colored bottles or bottles with lettering or coloration. In addition, the invention disclosed in the '784 patent could not accurately inspect the bottoms of round bottles. It therefore has been found that none of the monitoring systems currently being used are completely satisfactory in providing a system which has the necessary accuracy, reliability, versatility and/or speed required for today's modern methods of mass producing articles of manufacture and more specifically, glassware.

It therefore is an object of the present invention to provide a new and improved method and apparatus for monitoring and detecting defects in articles of manufacture such as glassware which is more dependable and accurate than those found in the prior art.

Another object of the present invention is to provide a new and improved method and apparatus for electronically monitoring and detecting defects in glassware having lettering, seams and/or other normal imperfections.

Yet another object of the present invention is to provide an improved method and apparatus for detecting flaws in colored glassware wherein both the sides and the bottom of the glassware may be inspected but wherein lettering, mold marks, coloring and minor imperfections are discriminated with respect to flaws in the glassware.

SUMMARY OF THE INVENTION

Accordingly, this invention relates to a method and apparatus for detecting defects in articles of manufacture, such as glassware, wherein semi-diffused light is directed through the article to be inspected and onto a video camera wherein the camera produces for each scan line a video signal indicative of the spatial rate of change of optical refraction characteristics of that portion of the article scanned. Means are provided for limiting the detected portion of the video signal received from the camera to a preselected window area. The detected portion of the video signal is filtered by a delay line to eliminate noise and signals produced by long perturbations in the article such as seams from being considered as defect representative signals. The filtered video signal is then coupled to a peak detector means for discriminating between the desired refraction characteristics of the article such as produced by lettering, seams and coloration and undesirable flaws, such as produced by spikes or birdswings. Means is also provided for discriminating between minor defects and defects serious enough to warrant inspection of the article being inspected. The resulting anomaly or defect signals are coupled to a logic means which includes a classifying circuit to assure that the defect signal was generated as a result of a defect in the article being inspected with the output of the logic means being utilized to energize a reject gate mechanism for inspecting the article.

BRIEF DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE PREFERRED EMBODIMENT

Figure 1:
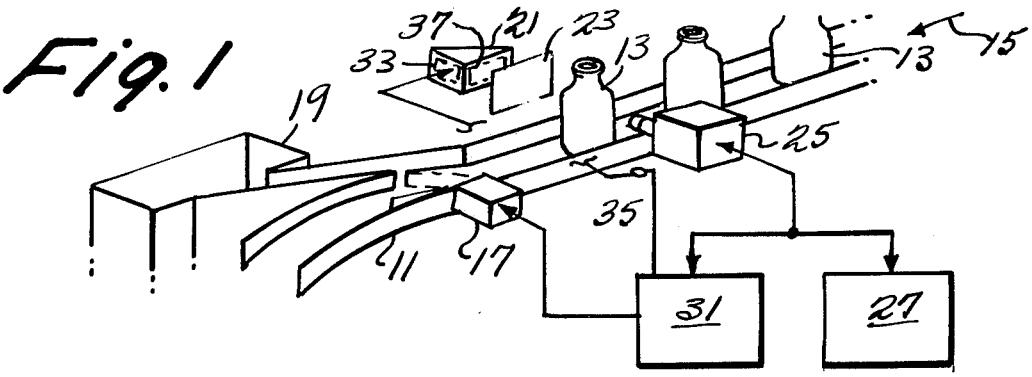
FIG. 1 is a partial perspective view and partial block diagram of an electronic video defect detection assembly constructed in accordance with the preferred embodiment of the present invention and preferably provided for detecting defects in a train of glass bottles transported along a conveyor mechanism.

Turning now to the drawings wherein like components are designated by like reference numerals throughout the various figures, the electronic inspection system of the present invention is disclosed. Referring to FIG. 1, there is illustrated a conveyor mechanism 11 positioned between various components of the electronic video inspection apparatus of the present invention for transporting a train of glassware, such as for example, glass bottles 13 past the assembly in the direction indicated by the arrow 15. The glassware may be in the form of round bottles or flasks and the bottles may be of any desired shading or coloration and in fact, by suitable modification of the preferred embodiment, as set out hereinbelow, opaque bottles or articles of manufacture can be inspected for defects if desired.

As each bottle passes the inspection assembly it is inspected for defects or abnormalities generally such as, for example, spikes or birdswings. In the event a defective bottle is detected, the electronic video assembly actuates a reject gate 17 positioned downstream of the assembly for directing the defective bottle away from the conveyor mechanism and into a reject platform or container 19. In this manner only the acceptable bottles are allowed to reach their ultimate destination on the conveyor mechanism for further processing. While a reject gate and platform or container are illustrated, it should be understood that any suitable reject means for removing a defective bottle from the conveyor may be provided. Thus, for example, a pushout arm (not shown) may be utilized for pushing the defective bottle off of the conveyor mechanism.

As illustrated in the figure, the electronic video assembly includes a semi-diffused light source 21 positioned on one side of and in close proximity to the conveyor mechanism 11 for illuminating each of the glass bottles 13 as the bottles pass thereby.

The semi-diffused light source is designed to illuminate each part of the object under inspection with a limited bundle of light rays. That is, the rays act neither as though they originated at a point source, as in a shadow graph, nor from a truly diffuse illuminant. The solid angular extent of the illuminating ray bundle at any point in the object plane determines the sensitivity of the optical image to changes in the refraction of the object under inspection. The smaller the ray bundle, the less therefraction change in the object under inspection needed to move the majority of the bundle out of the acceptance aperture of the camera imaging lens. The converse is true when the ray bundle subtends a larger solid angle. The greater the portion of the bundle through any point which escapes the acceptance aperture of the camera lens, the darker that point appears in the image. In the preferred embodiment of this invention the extent of the ray bundle through each point is designed to more than fill the acceptance aperture of the imaging lens.

The limited ray bundle passing through each point can be obtained from a diffuse source at a considerable distance from the object, or an optical system imaging an extensive source upon the camera lens, or other optical means.

It should be noted that a more uniform distribution of light rays can be obtained if the semi-diffused light source is positioned further away from the passing bottles. This, however, is not practical when the electronic video assembly is utilized in the typical glass manufacturing plant where space is at a premium. Accordingly, to solve this problem an optical distance producing lens 23 may be mounted between light source 21 and the conveyor mechanism 11. The optical distance producing lens which may be of any conventional design directs the light rays emanating from the source 21 onto and through the passing bottles 13 as if the light source 21 were substantially further away from the conveyor mechanism to thereby provide for a more uniform light distribution through the bottles 13.

A video camera 25 which is positioned on the side of the conveyor mechanism 11 opposite the light source 21 and in alignment therewith is provided for scanning each of the passing illuminated bottles so as to produce a representative standard video signal which, if desired, may be applied to a standard video monitor or display tube 27. At this point it should be noted that sudden changes in the refraction characteristics of the glass bottle being examined causes the light passing through these regions to be deflected in radically different directions compared to the direction of refraction of the light by the surrounding material forming the glassware. As a result in those regions where the glass has perturbations such as flaws, changes in thickness, lettering, etc., the light passing therethrough appears darker than in those regions displaying uniform thickness as do darker colored defects and occlusions. Accordingly, the image of the detected bottle on a screen 29 (illustrated in FIGS. 2a and 2b) of display tube 27 includes dark areas representing the rapid change in thickness of the detected bottle's leading and trailing edges hereinafter referred to as edges 1 and 2, abnormalities such as the birdswing defects illustrated, desired changes in thickness of the bottle caused by seams and lettering, changes in coloring of the bottle, and any foreign objects on or in the bottle.

It should be understood that the video display tube 27 is not required for the proper operation of the electronic bottle inspection apparatus of the present invention. However, it may be of significant aid in initially calibrating the system and will be of assistance in understanding the operation of the system as will be seen hereinbelow.

The video signal produced by camera 25 is also directed to electronic circuits for processing the video signals as indicated by the reference numeral 31 which circuits act upon the video signal to isolate signals representative of defects in the glassware being inspected. When a defect signal is detected, which signal must meet certain criteria to be explained hereinbelow, the processing circuit 31 generates a reject signal which is applied to the reject gate 17 for actuating the reject gate and deflecting the defective bottle onto the reject platform 19.

As previously disclosed in the U.S. Pat. No. 3,746,784 of Van Oosterhout and assigned to the common assignee herewith, apparatus is provided for overcoming the distortion of the video camera's output due to the movement of the bottles 13 past the cmaera 25. Thus, it has been found that as the bottles 13 move past the camera 25, there is a slight distortion of the camera's video output signal causing, for example, a blurred image to appear on the screen 29 of the video monitoring tube 27. The blurred image can possibly lead to slight inaccuracies in the detection of defects in bottles. Therefore, in accordance with the present invention, the semi-diffused light source 21 may be provided with a strobe mechanism 33 illustrated schematically in the figure for energizing and instantaneously thereafter deenergizing the light source 21 in response to the appearance of a bottle 13 in front of the light source. This is accomplished by positioning a photoelectric detecting device, such as a photocell, and light emitting diode (illustrated schematically in the figure by the numeral 35) in a position such that as the passing bottle comes into direct alignment with the light source 21 and the camera 25, a signal is generated for energizing the strobe mechanism. Since for each passing bottle the light source remains energized for a period of time which is quite small compared to the rate of movement of the bottles, camera 25 in effect sees a motionless object. Accordingly, video signal distortion caused by the moving bottles is eliminated.

A further improvement may be provided wherein a black mask 37 constructed, for example, of ordinary black construction paper, may be centrally positioned on the face of the diffused light source 21 as illustrated by the dotted lines in FIG. 1 so that only a slight peripheral portion of the light source's face is exposed. The light rays emanating from the peripheral portion, if desired, may then be polarized and/or directed toward the passing bottle. By utilizing this type of black mask approach, the illumination effect on the passing bottle is a reversal of the effect described above. In other words, the edges and defects of each illuminated bottle appear bright when some rays scatter into the lens aperture while the remaining portion thereof appears dark. It has been found that by using the white defect on black background approach as opposed to the black defect on white background approach, greater monitoring and detecting accuracy of diffusing defects can be achieved. However, for the purposes of describing the preferred embodiment of the present invention so as to provide a more clear and concise description thereof, it will be assumed that the black-on-white approach is being followed, it being readily apparent that both approaches are contemplated by the present invention.

Figures 2A, 2B:
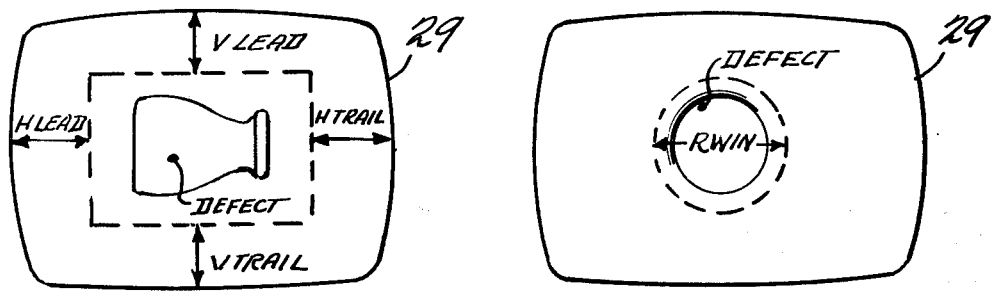
FIG. 2a is a front view of a standard television monitoring screen which may comprise part of the electronic video assembly illustrated in FIG. 1, which figure illustrates the square window timing feature of the present invention.
FIG. 2b is a front view of a standard television monitoring screen showing the round window timing feature of the present invention.
Figure 3:
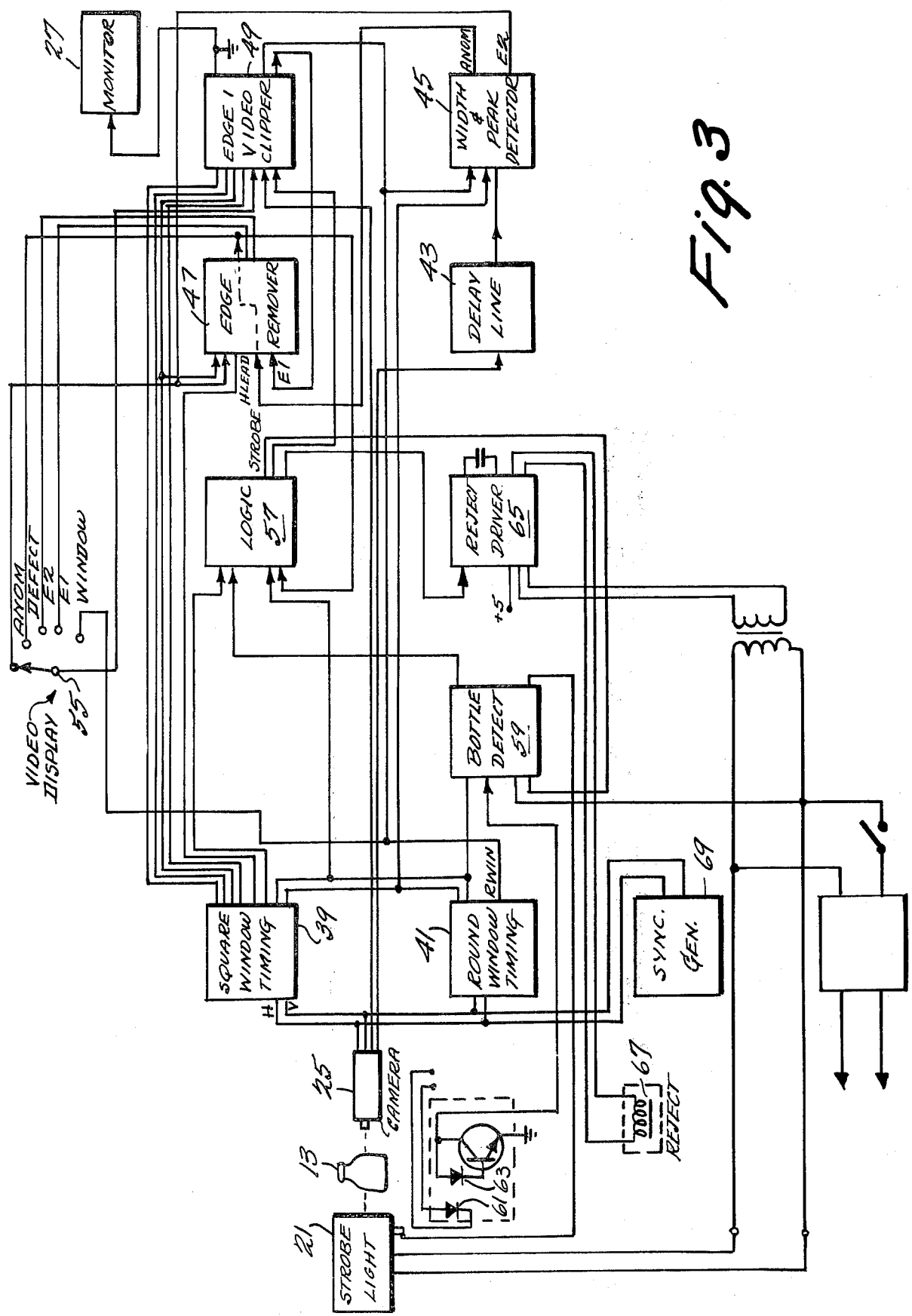
FIG. 3 is a block diagram of the component circuits making up the preferred embodiment of the video inspection apparatus of the present invention.

Refer now to FIG. 3 which is a schematic block diagram of the processing electronics of the preferred embodiment of the present invention. As illustrated in this figure, horizontal and vertical sync pulses, which comprise part of the composite video signal developed by camera 25, are applied to a square window timing circuit 39, a round window timing circuit 41 and to the video camera 25 by a video sync generator 69 of conventional design. As will be described more fully hereinbelow, the square window timing circuit generates a series of complex blanking signals hereinafter referred to as HLEAD, $\overline{\text{HLEAD}}$, HTRAIL, $\overline{\text{HTRAIL}}$, VLEAD, $\overline{\text{VLEAD}}$, VTRAIL and $\overline{\text{VTRAIL}}$. These signals, as will be explained, are provided mainly as reference signals for the overall operation of the electronic inspection apparatus of the present invention. As illustrated in FIG. 2a, the square window timing circuit 39 generates blanking pulses such that the video output signal of camera 25 is not processed to extract defect representing signals therefrom over that portion of the camera scan designated by the terms HLEAD, HTRAIL, VLEAD and VTRAIL.

The round window timing circuit 41 generates blanking signals such that, as illustrated in FIG. 2b, the video signal is processed for defect representative signals only when the camera scan is in the region defined by RWIN. The round window timing circuit is utilized when the bottom of a round, or other area defined as a conic section bottle is being inspected; whereas, the square window timing signals are utilized when the side walls of the bottle are being inspected. In the preferred embodiment of the present invention, only the square window timing or the round window timing is utilized at any given instant and accordingly, switches (not shown) may be provided for connecting one or the other of the timing circuits into the system of the present invention.

The video output signal of camera 25 is coupled to video detector circuitry which generally includes a delay line amplifier 43 and a width and peak detector circuit 45. The delay line amplifier in effect acts as a filtering means for filtering out video signals representing changes in the refraction of the light passing through the bottle being inspected when the change in amplitude of the video signal extends over a predetermined period of time. Thus, slow changes in the amplitude of the video signal caused by subtle waves or contour changes in the glassware being inspected, changes in coloring of the bottle, or elongated seams are eliminated by the delay line circuit 43 so that such changes in contour of the bottle being inspected are not detected as defects in the bottle.

The delay line amplifier 43 in effect acts as a filtering means which enhances the defect-like signals as compared with non-defect signals. The filtering effect is achieved by the weighted algebraic summation of successive time samples of the signal tapped off an analog delay means. It should be understood that total time delay, number of successive sammples, and sample weights can be adjusted to optimize the desired signal output. In the preferred embodiment the samples and weights have been chosen to yield a response equivalent to an averaged time differential response across a short portion of a single horizontal line.

The output of the delay line 43 may be coupled to the width and peak detector circuit 45 which generates a signal corresponding to a running average signal level of the output of the input signal.

The reference signal developed by the peak detector is a weighted running average of the input signal. The weighted average is developed by an assymetrically slew limited gated amplifier. Slew rate can be independently adjusted for positive and negatives signals. Thus, the weighted average reference can be made more or less responsive to positive or negative signal excursions. It is contemplated that any combination of positive and negative slew rates may be utilized to enhance detection of certain defects. In the preferred embodiment the positive slew rate is set to be much less than the rate of chance of defect signal and the negative slew rate is set to be much less than the positive slew rate. In effect, the slew limited reference acts like a peak detector.

This average signal is compared with the instantaneous output of the delay line 43 to provide a defect pulse whenever the difference between the average input signal level and the instantaneous delayed input signal level exceeds a predetermined level. The width and peak detector establishes a reference signal against which the defect representing video pulses are compared. This reference is the average DC level of the video signal over one horizontal line scan thereof. As the light intensity detected by the camera 25 appears to change due to bottle shading or coloration or misadjustment of the light source 21, or electronic component drift, the average video level correspondingly changes. Thus the processing circuits of the present bottle inspecting apparatus are not affected if the video level at the output of camera 25 shifts over relatively long periods of time. In addition, the width and peak detector includes a means for generating a defect or birdswing candidate signal only when the duration of the dark spot or defect pulse exceeds a predetermined time interval. This insures that only serious defects will result in actuation of the reject gate 17.

The defect or birdswing candidate pulse output of the width and peak detector circuit 45, which is designated the anomaly (ANOM) output, is coupled to the edge remover circuit 47.

An an ancillary feature, the width and peak detector circuit detects the positive going pulse generated by the camera 25 when the scanning beam scans past the trailing edge (edge 2) of the bottle being inspected. This signal is coupled to the edge remover circuit 47.

Before discussing the function of the edge remover circuit 47, attention is directed to the nature of the output of the video camera 25 when the sides of the bottle are being inspected for defects. As the camera 25 scans over an illuminated bottle 13, a first spiked pulse is generated which represents the first or leading edge of the bottle (edge 1). As the camera continues to scan over the bottle, one or more intermediate pulses may be generated which represent a defect such as, for example, a birdswing. However, it should be understood that the present invention contemplates any type of abnormalities which would cause an abrupt change in the refraction of the light rays passing through the detected bottle or in the case of an opaque object, a change in the intensity characteristics thereof, it being understood that smooth changes in the refraction of light are not detected because of the filtering provided by the delay line 43 and the peak and width detector 45. Finally, as the camera scans past the trailing edge (edge 2) of the bottle, a final spiked pulse is generated. Since the first and last spiked pulses occur because of normal changes in the refraction of the bottle, i.e., because of the leading and trailing edges of the bottle under examination, these pulses must be eliminated from the output of the camera so that the bottle being inspected is not rejected. Accordingly, the output of the camera 25 is coupled directly to the edge/video clipper circuit 49. The edge/video clipper circuit 49 includes a buffer amplifier and a gated comparator, as will be seen hereinbelow, which respond to the video signal so as to produce a negative going spiked pulse each time a dark spot on the detected bottle occurs. The negative going spiked pulses are coupled to the edge remover circuit 47. In addition, the edge/video clipper circuit 49 includes a circuit for selectively coupling the output of the camera 25 to the monitor 27 which, as aforementioned, is a television picture tube. The negative going spiked or dark spot pulses produced at the output of the edge/video clipper circuit 49 and the width and peak detector circuit 45 are applied to the edge remover circuit 47 which, as will be described hereinbelow, suppresses the spiked pulses representing edge 1 and edge 2 of the detected bottle and produces a negative going anomaly pulse (ANOM) representing a defect such as a birdswing. In addition, the edge remover circuit 47 provides edge 1 and edge 2 output signals which are coupled to a switch 55 of conventional design. The switch 55 is a video display switch wherein the edge 1 or edge 2 signals, among others, can be coupled to the video monitor 27 via the edge 1 clipper circuit 49 for close examination, if desired.

The anomaly output of the edge remover circuit 47 is coupled to the input of the logic circuit 57. The logic circuit 57, as will be more fully explained hereinbelow, receives the anomaly signal and produces an output reject signal if the following requirements are met: First, that a bottle or other article under observation is in fact being detected during a given period of detection; and second, that an abnormality, such as a birdswing, is in fact detected. In order for the logic circuit 57 to determine whether a bottle is in fact being detected, a bottle detect circuit 59 is provided wherein a light emitting diode 61 generates a light beam which is directed against the bottles 13 as they pass in front of camera 25. The light beam is reflected onto a photocell 63 by the passing bottles. The photocell provides a pulse to the bottle detector circuit 59 when the light ray passing therebetween is reflected by a bottle 13 being passing inspected. When a bottle is thus detected, a pulse is generated in the bottle detector circuit 59 and can be coupled to the strobe light 21 for momentarily illuminating the bottle 13. At the same time a bottle detect output pulse is coupled to the logic circuit 57 to indicate that the camera 25 is in fact detecting a bottle. It should be understood that by simple modification of the bottle detection circuit 59, the light emitting source could be positioned on the opposite side of the glassware being inspected from the photocell. In such a case, a bottle detection and strobe pulse would be generated when the light beam is interrupted.

The logic circuit 59 includes a classifying circuit which is activated only when a bottle detection pulse is coupled to the logic circuit 57. The classifying circuit provides a reject output signal when a defect appears during any given period of detection over a selected number of scan lines. Thus, for example, instead of classifying a bottle as defective after defect pulses have appeared on three or four consecutive scan lines, the operator may wish to classify a bottle as defective in the event a defect pulse appears in two of three consecutive scan lines, three of three consecutive scan lines, and so on. The generated reject pulse is then time delayed by circuitry to be explained hereinbelow in order to give the bottle under inspection time to approach the reject gate 17. The reject pulse is then coupled to a reject driver 65 which generates a curreent pulse which is coupled to the gate actuating solenoid 67 of the reject gate 17.

In the preferred embodiment, the sync generator 69 is of conventional design and provides horizontal and vertical television sync pulses for operating the video camera 25 and for driving the square window timing circuit 39 and the round window timing circuit 41. In addition, the voltage supply is derived from a standard 117 VAC line with standard rectifier and regulator circuits providing the various supply voltages required by the circuitry of the inspection apparatus of the present invention. Further, in keeping with the present invention, it should be understood that the aforementioned circuit components minus the square window timing circuit may be combined in a separate unit to provide an apparatus for inspecting round objects such as the bottoms of round bottles. Conversely, the aforementioned circuit components minus the round window timing circuit 41 may be combined in a separate unit to provide an apparatus for inspecting objects having noncircular shapes. In the embodiment illustrated, the square window and round window timing circuits 39 and 41, respectively, are combined in a single unit, it being understood that suitable switches (not shown) must be provided for switching one or the other of the timing circuits into the system at any particular time.

Figure 4:
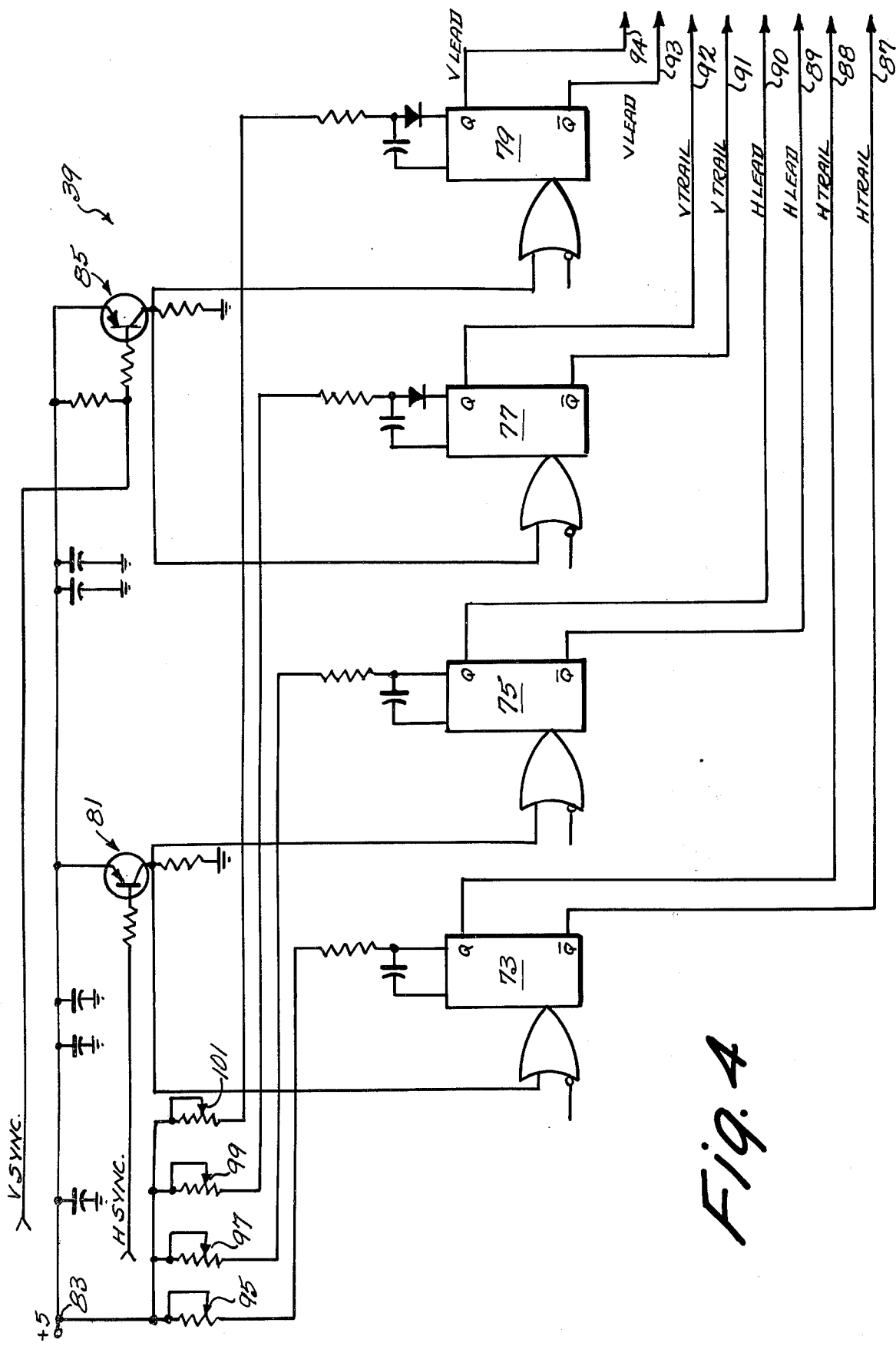
FIG. 4 is a detailed schematic of a preferred embodiment of the square window timing circuit utilized in the inspection apparatus of the present invention.

Refer now to FIG. 4 which is a schematic diagram of the square window timing circuit 39 of the present invention, which circuit determines the area of scan illustrated in FIG. 2a which will be processed by the detection circuitry 31 for inspecting sides of bottles of any desired shape or size including round bottles and flasks. The signals for defining the inspection area illustrated in FIG. 2a include eight reference signals HLEAD, $\overline{\text{HLEAD}}$, HTRAIL, $\overline{\text{HTRAIL}}$, VLEAD, $\overline{\text{VLEAD}}$, $\overline{\text{VTRAIL}}$, VTRAIL. The circuitry illustrated in FIG. 4 uses standard integrated monostable multivibrator circuits 73, 75, 77 and 79. Turning to FIG. 4, the horizontal synchronization pulses provided by the sync generator 69 are applied to the inputs of the monostable circuits 73 and 75 through an amplifier stage 81, which is driven by a five volt supply coupled to terminal 83. The vertical synchronization pulses provided by the sync generator 69 are applied to the inputs of monostable circuits 77 and 79 through an amplifying stage 85 which is also driven by the 5-volt power supply coupled to input terminal 83.

The monostable circuits 73 and 75, which are driven into their metastable states for a predetermined period of time by the horizontal sychronization pulses, are respectively responsible for the production of HTRAIL, $\overline{\text{HTRAIL}}$, HLEAD, and $\overline{\text{HLEAD}}$ at output terminals 87–90. The monostable circuits 77 and 79, which are driven into their metastable states for a predetermined period of time by the vertical synchronization pulses, are respectively responsible for the production of VTRAIL, $\overline{\text{VTRAIL}}$, VLEAD and $\overline{\text{VLEAD}}$ at output terminals 91–94, as illustrated. The timing of each of the monostable circuits 73, 75, 77 and 79 may be appropriately adjusted by respectively connected potentiometers 95, 97, 99 and 101 which are connected to the multivibrators 73–79 in a known manner to vary the timing thereof. Thus, with the reference to FIG. 2a of the drawings, by appropriately varying the tap of the potentiometer 95, the duration of the metastable state of the monostable circuit 73 can be varied to increase or decrease the duration of the HTRAIL portion of the horizontal scan. At the same time by appropriately adjusting the center tap of the potentiometer 97, the time duration of the metastable state of the monostable circuit 75 can be appropriately adjusted to vary the time duration of the HLEAD portion of the horizontal scan. Thus, it can be seen that by varying potentiometers 95 and 97, the width of the detection area scanned by the cameral 25 can be appropriately adjusted depending upon the width of bottles being inspected. In a similar manner, the potentiometers 99 and 101 can be appropriately varied to vary the height of the scanning area in accordance with the height of bottles being inspected.

As will be described in more detail hereinbelow, when any of the signals $\overline{\text{HLEAD}}$, $\overline{\text{HTRAIL}}$, $\overline{\text{VLEAD}}$ and $\overline{\text{VTRAIL}}$ are low, the width and peak detector circuit 45 is inhibited from responding to the video output of camera 25, thereby effectively creating a limited field of detection. This may thus be exemplified by screen 29 of the video display tube 27 illustrated in FIG. 2a wherein the portion of the video scan coupled to the width and peak detector 45 for detection of defects is illustrated by the dotted lines. The area within the window represents the field of detection of the video assembly while the area surrounding the window represents the time in which VLEAD, VTRAIL, HLEAD and HTRAIL are high.

Figure 5:
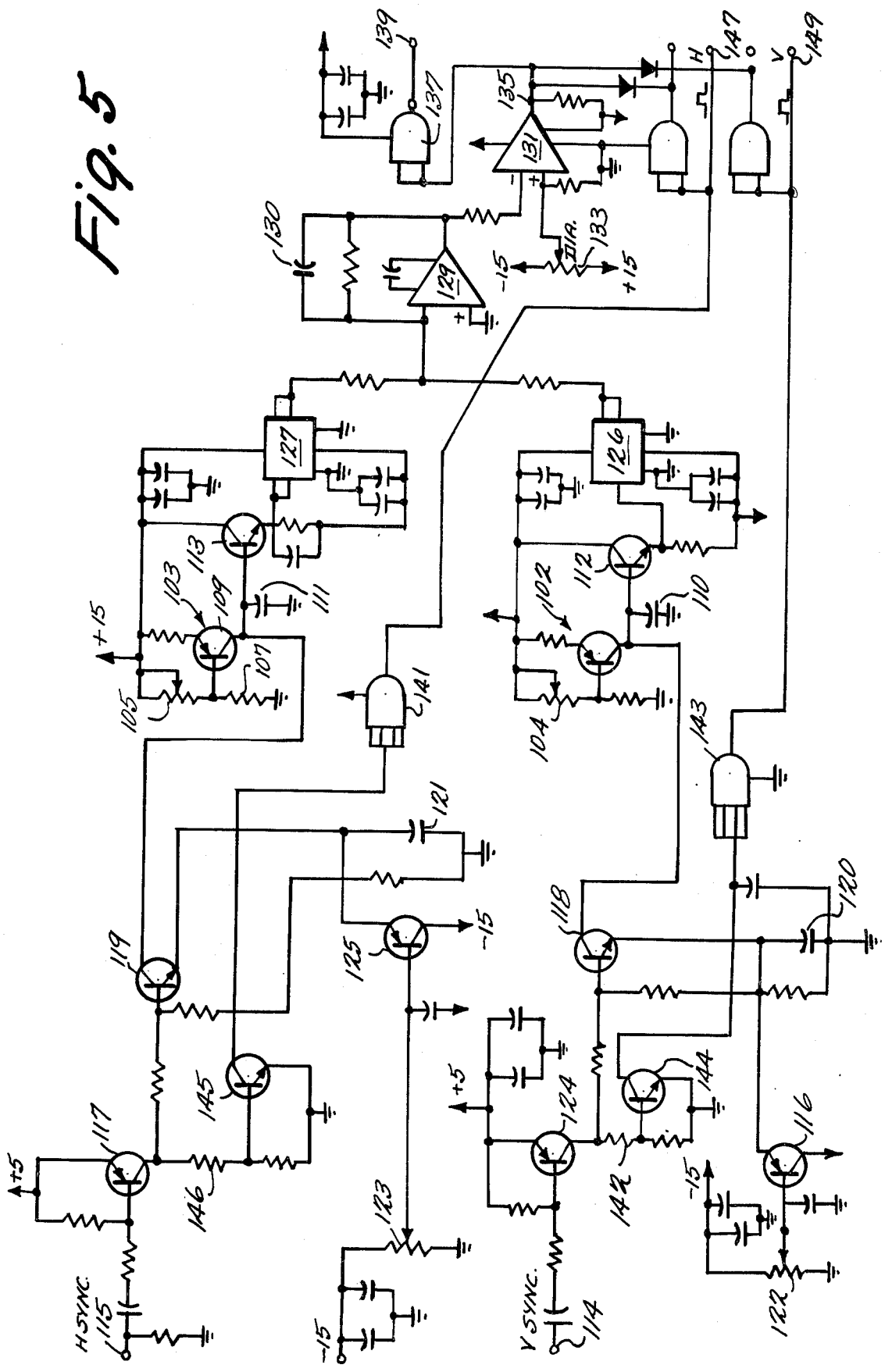
FIG. 5 is a detailed schematic of a preferred embodiment of the round window timing circuit utilized in the present invention.

Refer now to FIG. 5 which is a detailed schematic diagram of the round window timing circuit 41 of the present invention. This circuit is provided in case it is desired to inspect the bottoms of round jars and bottles or other round objects. Thus, the round window timing circuit 41 generates a video detection area, such as illustrated in FIG. 2b, which is circular in shape. To generate such a window, the following equation must be satisfied:

$$x^2 + y^2 = k$$

wherein $x$ is the horizontal distance from an origin which is at the center of the round window, $y$ is the vertical distance from the origin, and $k$ is a constant which determines the size of the window. In order to generate the $x$ function, a constant current generator, generally designated by the numeral 103 and including variable resistor 105 and resistor 107 together with transistor 109, generates a constant current having a magnitude determined by the setting of the variable resistor 105. The output of the constant current generator 103 is coupled to charging capacitor 111 to thereby generate a horizontal ramp function which is coupled to the input of transistor 113. In order to establish a reference voltage across the capacitor 111 at the beginning of each horizontal scan interval, so that the generated ramp function increases linearly about a zero voltage level, circuitry is provided to set the charge on capacitor 111 at the beginning of each horizontal scan interval. A horizontal sync pulse is coupled to input terminal 115 to turn on transistor 117 which in turn causes transistor 119 to be turned on. Hence, capacitor 111 is directly coupled to capacitor 121 which is of a substantially greater capacitance value than capacitor 111. Thus, capacitor 111 discharges until its voltage equals the voltage across the capacitor 121 to thereby establish a reference voltage level at the input to transistor 113 at the beginning of each horizontal scanning interval.

The reference voltage or charge on the capacitor 121 is determined by adjusting the center tap of potentiometer 123. Thus, by varying the position of the center tap of potentiometer 123, the output of transistor 125 is varied to thereby vary the output voltage across the capacitor 121 to the level desired. By varying the charge on the capacitor 121, the horizontal position of the window illustrated in FIG. 2b can be varied as desired.

The ramp function generated by the constant current generator 103 and the capacitor 111 is amplified by transistor 113 which is in the emitter-follower configuration. The output of transistor 113 at the emitter thereof is coupled to multiplier 127 wherein the ramp function signal is multiplied by itself, i.e., squared. The multiplier 127 may be of any conventional design but in the preferred embodiment is an integrated transconductance multiplier. The squared output of the analog multiplier 127 is then coupled to a summing amplifier 129.

A similar circuit for generating a ramp function in response to a vertical sync pulse and then squaring the ramp function is also provided. Thus, a constant current generator 102 is provided having an output current level which is dependent upon the setting of variable resistor 104. The output of the constant current generator 102 is coupled to charging capacitor 110 to thereby generate a ramp function which is coupled to the input of transistor 112. The reference charge level of the capacitor 11o is determined by the voltage level across reference capacitor 120. Thus, when a vertical sync pulse is generated, it is coupled to input terminal 114, amplified and coupled to the input of transistor 118. Accordingly, transistor 118 turns on, thereby connecting charging capacitor 110 directly across reference capacitor 120. Thus the charge on the capacitor 110, which has a capacitance valve much smaller than that of reference capacitor 120 is set at a predetermined reference level depending upon the voltage across the capacitor 120. The voltage across capacitor 120 may be varied by means of potentiometer 122. Thus, depending on the position of the center tap of the potentiometer 122 which is connected to the base of transistor 116, the voltage across the capacitor 120 may be varied as desired to establish the vertical position of the round window illustrated in FIG. 2b. It should be pointed out that the charging current coupled to each of the capacitors 110 and 111 by the current sources 102 and 103, respectively, is varied to compensate for the 3:4 video aspect ratio of typical video systems.

The ramp function generated by the constant current source 102 and the charging capacitor 110 is then current amplified by transistor 112 which is in the emitter-follower configuration and is then squared by multiplier 126 which in the preferred embodiment is identical to multiplier 127. The squared output of multiplier 126 is summed together with the squared output of multiplier 127 in the summing amplifier 129. Amplifier 129 has a noise eliminating feedback capacitor 130 connected across the output and input terminals thereof. The output of summing amplifier 129 is coupled to a comparator 131. The other input to the comparator 131 is derived from the center tap of a potentiometer 133, which potentiometer establishes the diameter of the round window illustrated in FIG. 2b. Thus, by varying the voltage input to the comparator 131, the potentiometer 133 in effect varies the diameter of the round window illustrated in FIG. 2b. The output of the comparator 131 is negative during the window portion (RWIN) of each horizontal line scan and is positive outside of the window portion of the horizontal line scan.

Accordingly, at output 135 a negative going signal appears whenever the video camera is scanning inside of the round window illustrated in FIG. 2b and is positive whenever the scan of the video camera is outside of the window. This signal is inverted by NAND gate 137 to provide a positive going RWIN output at terminal 139 which signal is utilized in the width and peak detector circuit 45 in the manner explained hereinbelow.

The negative going horizontal and vertical sync pulses are converted to positive going horizontal and vertical sync pulses by means of NAND gates 141 and 143, respectively. Thus, for example, the negative horizontal sync pulse connected to input terminal 115 turns on transistor 117, thereby coupling a 5 volt supply voltage to the base of transistor 145 via resistor 146. Transistor 145 is thereby turned on, thereby forcing the input to NAND gate 141 low. The output of NAND gate 141 is therefore high which signal is coupled to the horizontal trigger output terminal 147. This signal is utilized in the peak and width detector in a manner to be described hereinbelow. In a similar manner, a negative going vertical sync pulse coupled to input terminal 114 turns on transistor 124, thereby connecting the 5 volt suppy voltage to the base input terminal of transistor 144 via resistor 142 to thereby turn on transistor 144. With transistor 144 turned on, the input to NAND gate 143 goes low, thereby causing the output of the NAND gate 143 to go high. This high signal is coupled to the vertical trigger output terminal 149 and may be used in the bottle detection circuit to synchronize the testing of the circuits of the present invention and in addition may be coupled to the logic circuit 57 for synchronizing the classification and strobe firing circuits therein.

Figure 6:
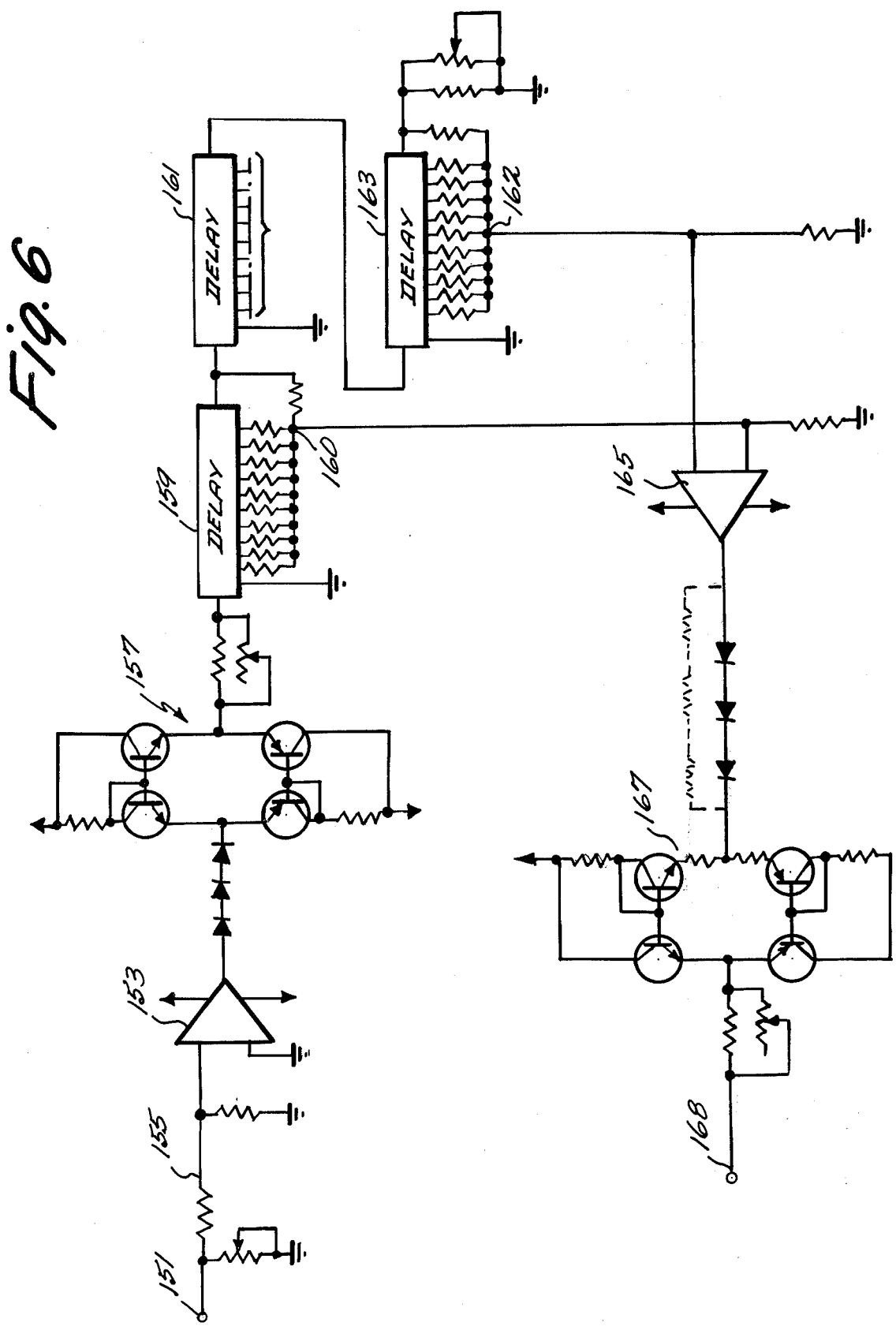
FIG. 6 is a detailed schematic diagram of the time delay circuit of a preferred embodiment of the present invention.

Refer now to FIG. 6 which is a schematic illustration of the delay line 43 of the present invention. The output of the video camera 25 is coupled directly to the input terminal 151 of the video delay line. The video signal is coupled to an impedance matching network including amplifier 153 via an impedance matching resistance network generally designated by the numeral 155. The output of the amplifier 153 is coupled to a complimentary symetry amplifier 157 of conventional design which serves as a low output impedance driver amplifier for the three delay line networks 159, 161 and 163. Each of the delay lines 159, 161, and 163 is of conventional design and in the preferred embodiment, are EL-RAD 65–293 delay lines. The first and third delay lines 159 and 163, respectively, have a series of ten output taps connected to common output points 160 and 162, respectively, via 10 k ohm resistors, with each tap representing a ten nanosecond delay. The output of each of the delay lines 159 and 163 is therefore the average of the input signal to the respective delay lines over 100 nanoseconds. This very effectively averages out the noise component of the video signal to the delay lines. Delay line 161 also provides a 100 nanosecond delay but does not have the signal averaging arrangement. The outputs of the first and third delay line 159 and 163, respectively, are coupled to the inputs of a differential amplifier 165 with there being a 100 nanosecond delay between the first and third delay lines. The output of the differential amplifier 165 is coupled to an output buffer amplifier 167 with the output of the buffer amplifier 167 being coupled to output terminal 168 to drive the width and peak detector circuit 45 as will be described hereinbelow.

For video signal pulses of less than 100 nanoseconds duration, the delay line circuit will provide two serial pulses at the output terminal 168. The reason for this is that since 100 nanoseconds represents the maximum length of a pulse which can be stored in one delay line, the following differential amplifier 165 will see the pulse first on one input from the delay line 159 and then 100 nanoseconds later on the other input from delay line 163, thereby resulting in two output pulses being generated by differential amplifier 165, one of opposite polarity to the other. In the preferred embodiment it has been selected that any pulse of less than 200 nanoseconds duration at the input 151 of delay line circuit is not a flaw in the glassware to be inspected. If the video signal pulse at the input to the delay line processer exceeds 200 nanoseconds duration, the differential amplifier will provide 100 nanoseconds pulse both at the start and finish of the input pulse. If these pulses start before inspection time and after inspection time, then no defect pulse will result during inspection time gating. Such a long duration pulse may result because of an edge, a flute or a seam in the glassware being inspected. Thus, only changes from dark to light or light to dark in the inspection area defined by the round window or square timing circuit results in reject timing pulses.

Since the differential amplifier 165 compares changes of signal amplitude only over a measured time interval, slow changes of signal amplitude such as those caused by subtle waves or contour changes in the glassware to be inspected do not develop output pulses of sufficient amplitude to be detected as defects by the width and peak detector circuitry 45.

Figure 7:
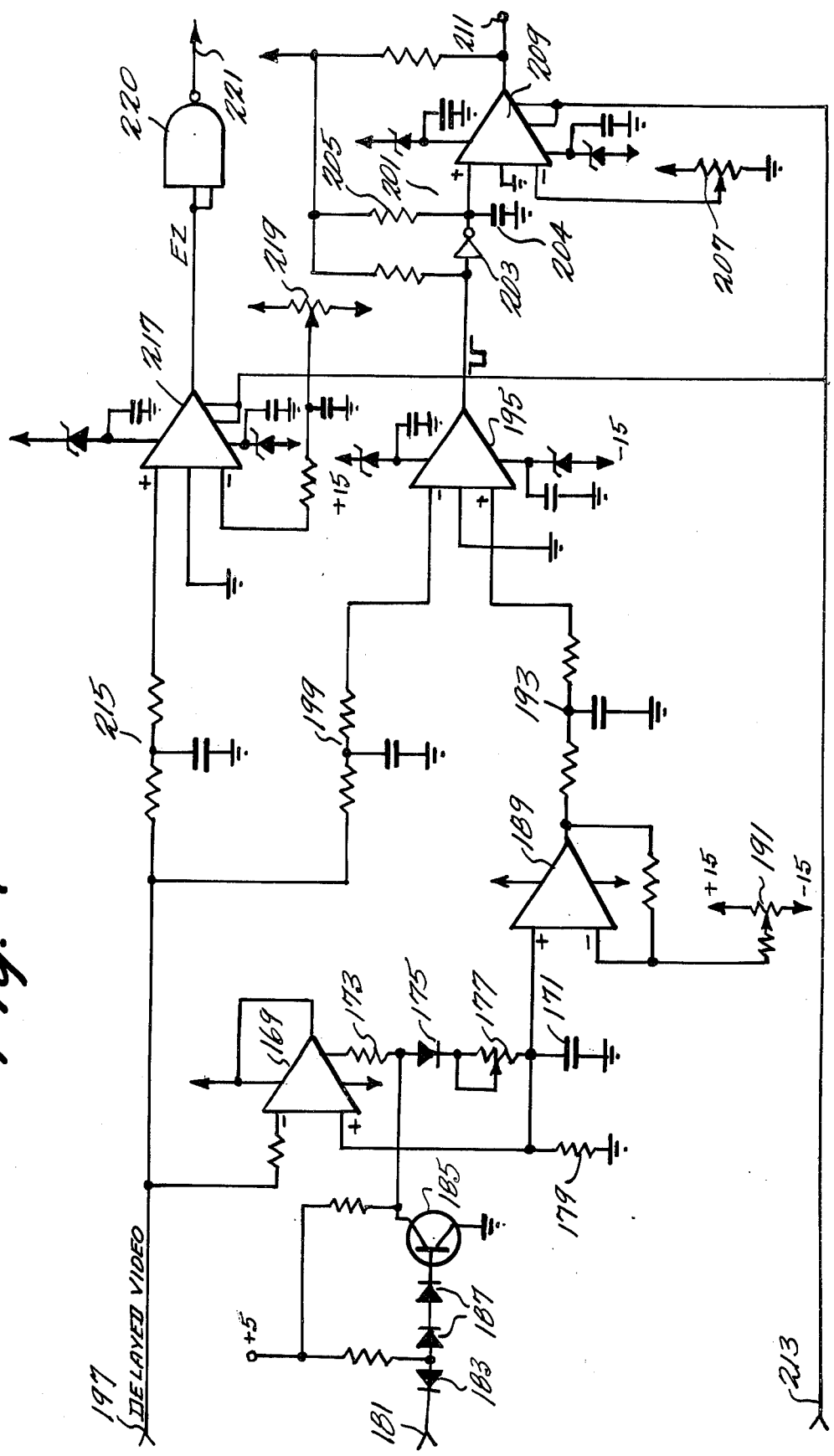
FIG. 7 is a detailed schematic diagram of the width and peak detector circuit of the preferred embodiment of the present invention.

Refer now to FIG. 7 which is a detailed schematic diagram of the width and peak detector 45 of the present invention. In order to obtain uniform accuracy over long periods of time and in changing temperature environments, a stabilized reference must be established against which video pulses representing defects are compared. The reference level selected is the average DC level of the video signal output of the camera 25 over a one horizontal line scan interval. Thus, as light intensity appears to change due to bottle shading or coloration, misadjustment of the light source 21, or electronic component drift, the video level also tends to change. Accordingly, peak detector circuit 45 compares the video signal pulses coupled thereto with the average video plus noise level over each horizontal line scan to thereby eliminate the effect of video level shifts over relatively long periods of time.

Referring to FIG. 7, comparator 169 compares the voltage level across capacitor 171 with the delayed video input signal from the video delay line 43. If the voltage level across the capacitor 171 is less than the video signal level coupled to the comparator 169, the comparator 169 generates an output signal for charging the capacitor 171 via resistor 173, diode 175 and variable resistor 177. Resistor 173 limits the rate of charge of capacitor 171, thereby limiting fast slewing amplitude changes of the video signal. Discharge resistor 179 discharges capacitor 171 at a set rate to permit the capacitor 171 to follow slow decreases in the average output level of the video camera 25 at a low negative slew rate.

In order to prevent the horizontal synchronization pulse from causing the capacitor 171 to charge, the horizontal trigger signal H generated by the round window timing circuit 41 or the HLEAD signal generated by the square window timing circuit 39 is coupled to input terminal 181. Thus, when the voltage at the input terminal 181 goes high, representing the occurrence of a horizontal sync pulse, diode 183 is back biased, thereby connecting the five volt source illustrated to the transistor 185 via forward biased diode 187. With transitor 185 turned on because of the 5 volts connected to the base thereof, the junction of resistors 173 and 175 is grounded, thereby prohibiting the horizontal sync pulse from affecting the charge on capacitor 171. The diode 175 prevents rapid discharge of the capacitor 171 through the turned on transistor 185. When, however, the horizontal sync pulse interval terminates, the horizontal trigger output of the round window timing circuit goes to ground potential and accordingly, the potential at input terminal 181 drops to ground potential, thereby causing diode 183 to become forward biased which in turn results in transistor 185 being turned off. Thus, the average video signal coupled to the input of the comparator 169 is again effective to charge or discharge capacitor 171 so that the voltage thereacross corresponds to the average video signal level.

The voltage level across storage capacitor 171 is amplified by a sensitivity level shifting amplifier 189 which also receives an input from potentiometer 191. The potentiometer 191 can be varied to vary the sensitivity of the circuit to changes in the average video signal level represented by the charge across the capacitor 171. The output of amplifier 189 is coupled via a low pass filter 193 to a comparator 195. Also coupled to the comparator 195 is the delayed video signal from the delay line 43 of FIG. 6 which is coupled to the comparator 195 via input terminal 197 and low pass noise filter 199. The output of comparator 195 is a negative going pulse when a defect is detected with the duration of the pulse depending upon the relative length of the defect in the glassware being inspected.

In order to determine whether a defect is serious enough to warrant rejection of the glassware being inspected, the defect pulse duration is measured by means of a pulsewidth discriminator circuit generally designated by the numeral 201. The negative defect pulse from the output of comparator 195 is inverted by inverter 203. Capacitor 204 charges via resistor 205 during the duration of the negative pulse output of comparator 195 since the inverter 203 is an open collector gate. The charge on capacitor 204 is proportional to the pulse duration since the capacitor is permitted to charge only during the time in which a negative output pulse is provided by the comparator 195. If the charge on the capacitor 204 exceeds a level set by the width potentiometer 207, the comparator 209 provides a pulse at its output terminal 211. It should be understood, however, that comparator 209 is gated to generate output defect pulses only during that portion of each horizontal scan interval which falls within the window defined by either the round window timing circuit 41 or the square window timing circuit 39. Thus, at input terminal 213, an input signal is coupled from the round window timing circuit 41 or from the square window timing circuit 39 via the edge video clipper circuit 49. The signal at input terminal 213 is coupled to the gate input terminal of the amplifier 209 to inhibit the amplifier from providing an output whenever the horizontal line scan is outside of the window, defined by the circuits 39 or 41.

The delayed video input at terminal 197 is also coupled via a noise filter 215 to a comparator 217. The comparison level in the comparator 217 is established by a potentiometer 209. Thus, any signals appearing at input terminal 197 having a value greater than that established by the potentiometer 219 are coupled via an inverter 220 to output terminal 221 which terminal is coupled to the edge remover circuit 47 for a purpose more fully explained hereinbelow. Since pulses coupled to terminal 197 should not be processed except during the window portion of the camera scan, the signal at input terminal 213 is also coupled to comparator 217 for inhibiting the caparator whenever the scan is outside the window defined by circuits 39 or 41. Now that the circuitry has been disclosed and described for discriminating between signals corresponding to rejectable defects in the glassware and signals corresponding to other normal variations in the glassware, the circuitry for processing the defect signals and the first and second edge signals will now be explained.

Figure 8:
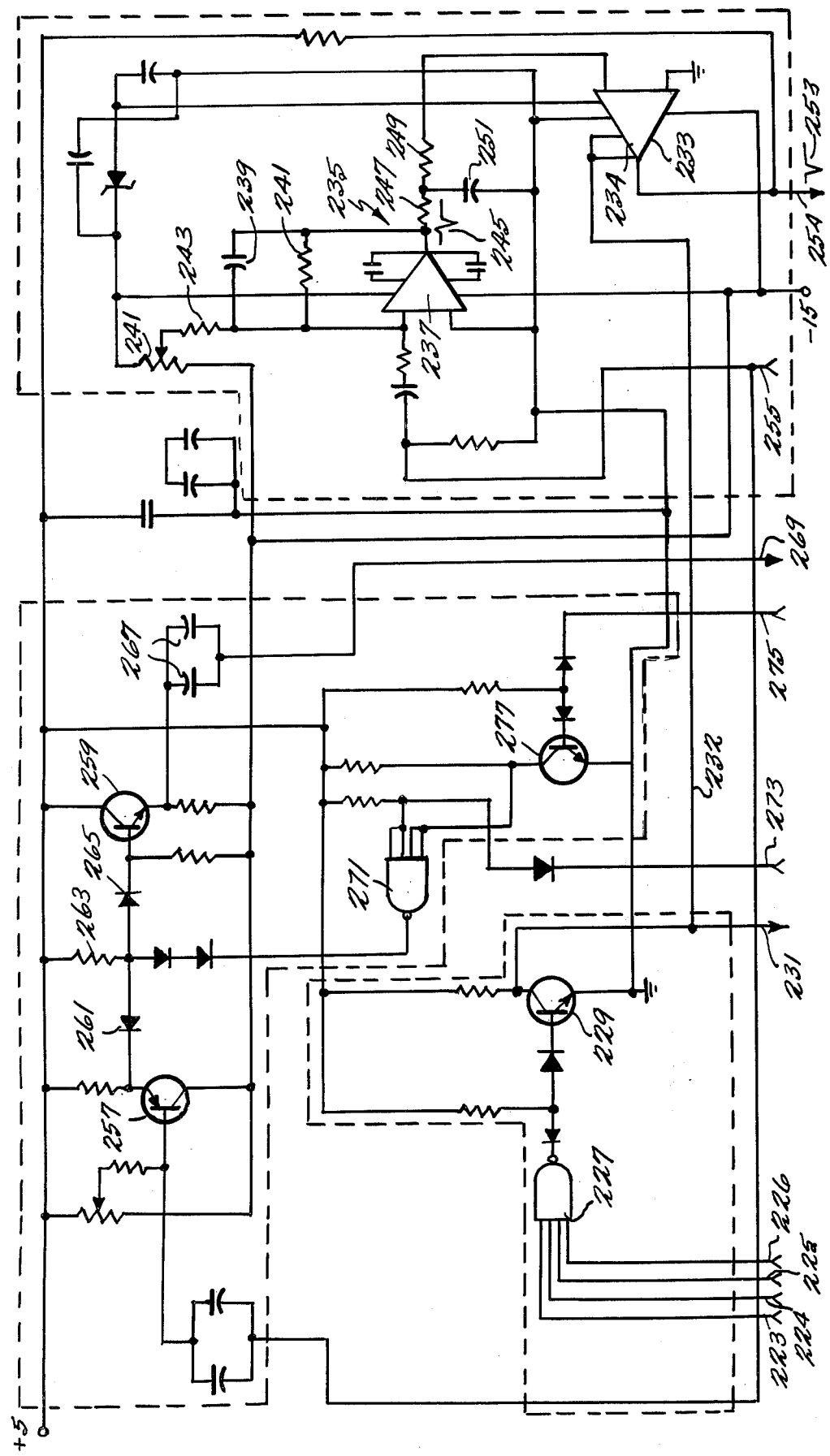
FIG. 8 is a detailed schematic diagram of the preferred embodiment of the edge video clipper circuit of the present invention.

Accordingly, refer to FIG. 8 which is a schematic diagram of a preferred embodiment of the edge clipper circuit of the present invention. Coupled to input terminals 223–226 are the signals $\overline{\text{VTRAIL}}$, $\overline{\text{HLEAD}}$, $\overline{\text{HTRAIL}}$ and $\overline{\text{VLEAD}}$, respectively, which are generated by the square window timing circuit 39. These signals are each coupled to a NAND gate 227 which provides a low output pulse for turning off transistor 229 whenever the signals $\overline{\text{VTRAIL}}$, $\overline{\text{HLEAD}}$, $\overline{\text{HTRAIL}}$ and $\overline{\text{VLEAD}}$ are each high. With transistor 229 turned off, the output at terminal 231, which is coupled to input terminal 213 of FIG. 7 to control or gate the comparators 209 and 217, goes high. Thus when the signal at the output terminal is high the comparators 209 and 217 are gated on. It should be understood that the RWIN output of the round window timing circuit 41 may alternatively be applied to the comparators 209 and 217 of FIG. 7.

In addition, the window timing signal is coupled to comparator 233 via line 232 in order to control the time during which comparator 233 operates.

Also coupled to the edge 1 clipper circuit of FIG. 8 is the video output signal of camera 25. This signal is connected to a buffer amplifier 235 for the purpose of detecting the leading edge of the glassware being inspected. The buffer amplifier includes operational amplifier 237, capacitor 239 and a resistor 241, the latter two of which are connected in parallel across the amplifier. A variable potentiometer 241 is also connected in circuit with the buffer amplifier circuit 235 and is connected to the input of the amplifier 237 through resistor 243 for adjusting the DC level of the amplifier output.

The buffer amplifier circuit tailors the incoming video signal so that sharp transitions appear at the output of the amplifier as large spikes, such as for example, spike signal 245 while slow transitions cause little if any response. In this manner the portions of the incoming video signal representing dark transitions in the detected bottle are enhanced and provide a suitable signal for the edge remover circuit 47. The spike signal 245 is applied through a filter stage comprising series connected resistors 247 and 249 and grounded capacitor 251 to the input of a comparator circuit 233. The comparator 233 in response to the spiked pulse 245 produces a negative going spike pulse 253. As mentioned hereinabove, this pulse appears at every sufficiently dark spot on the detected bottle as the latter is scanned by camera 25.

The comparator 233 is turned on or off by means of the output of the transistor 299. Thus, when each of the inputs $\overline{\text{VTRAIL}}$, $\overline{\text{HLEAD}}$, $\overline{\text{HTRAIL}}$ and $\overline{\text{VLEAD}}$ are low indicating that the horizontal scan is outside of the window area, the output of the transistor 229 is low. This low signal is coupled to the inhibit input terminal 234 of the comparator 233 to thereby inhibit amplifier 233 from generating an output pulse. However, when the output of transistor 229 goes high indicating that the camera scan is within the window, the positive going signal coupled to the inhibit input 234 of the comparator 233 enables the comparator to generate negative going output pulses whenever a dark spot is detected. This signal is coupled to the output terminal 254 of the circuit of FIG. 8. If in the alternative the round window timing is being utilized, the output at terminal 137 of the round window timing circuit illustrated in FIG. 5 is coupled to gate terminal 234 via input terminal 231. As aforementioned the switching circuit required for alternatively coupling square window or round window timing signals to the gated amplifiers is not disclosed herein since the arrangement of such switches would be well within the skill of one of ordinary skill in the art.

The edge one/video clipper circuit of FIG. 8 also includes a clipping display amplifier for controlling the video signal coupled to the monitor display 27. The video output of camera 25 is coupled to input terminal 255 and then to transistor 257. Transistor 257 is normally operating in its linear region. Transistor 259 is operating in its linear region due to the biasing current from resistor 263 and forward biased diode 265. Accordingly, the output of transistor 259 which is connected in an emitter-follower configuration is coupled via capacitors 267 to an output terminal 269 which is connected to the video monitor 27. However, when a negative going pulse from the video camera 25 is generated indicating the occurrence of a dark spot or change in refraction of the glassware under inspection, transistor 257 is turned on to thereby forward bias diode 261. Under this condition the biasing voltage at the gate of transistor 259 goes in a negative direction, thereby driving the output of transistor 259 in the negative direction. This negative going signal is coupled to the video output terminal 269 via the capacitors 267 and is then coupled to the video monitor 27 for display.

It may be desirable to display other signals on the video monitor 51 for purposes of circuit inspection, and to determine the relative positions of the first and second edge signals, the window generating signals, and the defect signal while viewing the remaining output signals generated by camera 25. To achieve this a NAND gate 271 is provided which when it generates a low output, drives the voltage at the base terminal of transistor 259 in the negative direction. Accordingly, the output signal to the video monitor 51 goes negative for the duration of the low output of the NAND gate 271, thereby clipping the video input signal at terminal 255 and superimposing a black image of these signals on the video display 27. In order to provide a low output signal at the output of NAND gate 271, two conditions must occur. First, a bottle must be under inspection and second, a signal representing the area of the video scan to be clipped must be generated. Accordingly, at input terminal 273 a high signal is provided whenever a bottle is being inspected. This high signal, as will be seen hereinbelow, is generated by the logic circuitry 57 shown in FIG. 3 and in detail in FIG. 10. In addition, at terminal 275 a signal representing the area to be clipped is provided. Thus, for example, assume that it is desirable to clip that portion of the video scan defined by the window signal. The window signal may be the square window signal provided at output 231 or may be the round window signal provided at the output of the round window timing circuit 41. This signal, when applied to input terminal 275 via video display switch 55 shown in FIG. 3, causes normally conducting transistor 277 to turn off whenever the window signal goes low. Thus, with transistor 277 turned off, a high signal is coupled to the input of NAND gate 271. With two high inputs to NAND gate 271, the output thereof goes low to thereby clip the video input signal at terminal 255. Thus the portion of the video scan outside of the window appears dark on the video monitor 51. It should be understood that other portions of the video output of camera 25 can be appropriately clipped by applying other signals to the terminal 275 via switch 55 as desired.

Figure 9:
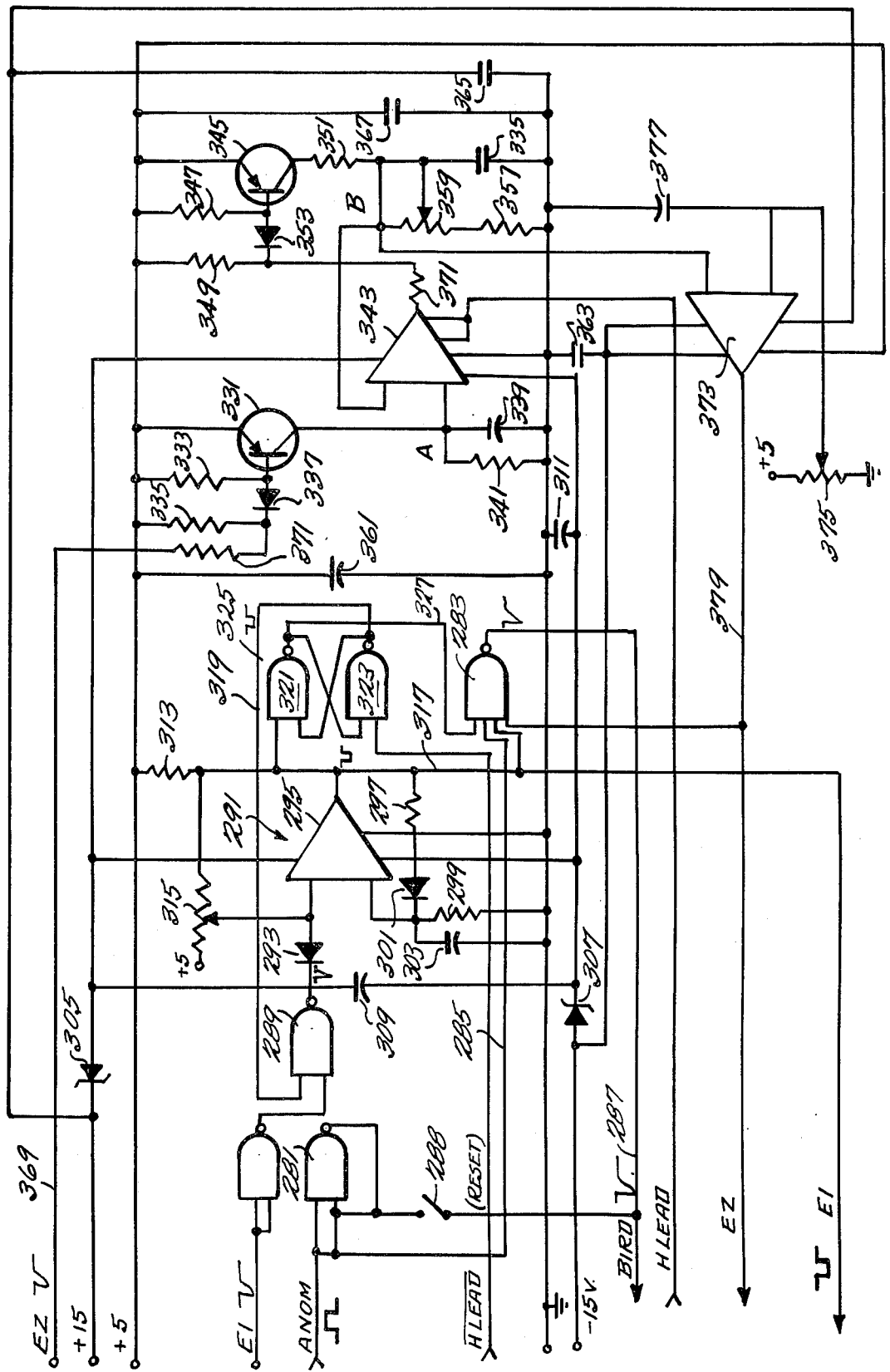
FIG. 9 is a detailed schematic illustration of the edge signal remover of the preferred embodiment of the present invention.

Refer now to FIG. 9 which is a detailed schematic illustration of the edge signal remover circuit 47 of the present invention which, as aforementioned, is provided for suppressing or removing from further processing those dark spot pulses representative of the edges of the bottle being scanned. The anomaly signal generated at the output of the width and peak detector circuits 45 is coupled to the input of a NAND gate 281 which serves as an inverter, the output of which is coupled to a second NAND gate 283 via lead 285. As will be seen hereinbelow, NAND gate 283 is inhibited from producing an output pulse in response to input pulses representing the leading edge (E1) and trailing edge (E2) of the bottle being detected, while on the other hand, producing an output defect or bird candidate pulse on lead 287 in response to those dark spot pulses representing a birdswing, spike or other such defect in the detected bottle.

The first pulse appearing on a given scan line after the end of the leading horizontal timing period, i.e., after the period when HLEAD is high or RWIN is low, is classified as the leading edge or E1 pulse of the bottle being detected. This first pulse is detected by the E1 detector circuit of FIG. 8 and is coupled from output terminal 254 of FIG. 8 to both inputs of a two-input NAND gate 288 which in response thereto, applies a high signal to one input of a two-input NAND gate 289. The output of NAND gate accordingly goes low. This low signal is applied to a high duty factor monostable multivibrator circuit 291 through a diode 293 for triggering the multivibrator circuit into its metastable state.

Monostable multivibrator circuit 291 includes a comparator 295, resistors 297 and 298, diode 301 and quick charging and slow discharging capacitor 303 and is driven by a positive 15 volt DC power supply through a voltage stabilizing zener diode 305 and a negative 15 volt DC power supply through a voltage stabilizing zener diode 307 with both of the power supplies being grounded through noise filter capacitors 309 and 311, respectively.

Upon being triggered into its metastable state by the initial edge one signal, multivibrator circuit 291 operates with a five volt source coupled to the output of the comparator 295 via resistor 313 to produce a low voltage signal E1. In this regard, the time in which the circuit is in its metastable state depends upon a potentiometer 315 connected at one end to the input of comparator 295 and at the other end to a positive 5 volt DC supply.

Output signal E1 is applied to a second input of NAND gate 283 via lead 317 and inhibits the NAND gate from producing an output signal in response to the first dark spot signal pulse representative of the first edge of the bottle being detected. In this manner the dark spot pulse representative of the first edge of the bottle being detected is removed from further processing.

The output signal E1 in addition to being applied to NAND gate 283 is applied to the input of a two-stage flip-flop 319 formed by dual NAND gates 321 and 323 which in response to the E1 signal is triggered into its set state and provides a low signal via line 325 back to the otherwise free input of gate 289. In this manner the NAND gate 289 is inhibited from allowing further dark pulses to reach multivibrator circuit 291. Accordingly, only the first dark spot pulse, that is, the leading edge pulse E1 on any given scan line will cause generation of the E1 signal. It should be noted that the output of gate 321 of the dual gate flip-flop 319 is also applied to NAND gate 283 via lead 327. As a result of this, NAND gate 283 is inhibited prior to the appearance of the E1 signal and the setting of flip-flop 319 for preventing the first dark spot pulse applied to lead 285 from triggering the NAND gate 283 in the event it reaches the NAND gate 283 before the E1 signal. As stated hereinbefore, flip-flop 319 is triggered into its set state by the first dark spot pulse appearing on a given scan line and remains in this state for the entire scan line period. During the beginning of the next scan line when $\overline{HLEAD}$ goes low, that is, before the window portion of the scan is reached, the flip-flop 319 is reset by the $\overline{HLEAD}$ signal which as illustrated is applied to gate 323 of the flip-flop. In this manner, the flip-flop is again ready to be triggered by the first dark spot pulse appearing on the next following scan line.

Attention is now directed to the manner in which the edge removal circuit 47 detects the trailing edge of the bottle being detected. In this regard, it is to be noted that the last dark spot pulse appearing on any given horizontal scan line is classified as the trailing edge or E2 signal of the bottle. This signal is detected by the width and peak detector circuit 45 and as will be seen hereinbelow this signal initiates a time delayed signal E2 each horizontal scan line which signal appears on the following horizontal scan line and inhibits NAND gate for a predetermined period during which the trailing edge dark spot pulse on the following line appears at the NAND gate 283. In other words, the circuitry required for eliminating the trailing edge dark spot pulse is a memory circuit which remembers where the trailing edge of the bottle being detected occurred on a previous line for suppressing a similar pulse on the following line. The circuitry required to accomplish E2 suppression includes a first transistorized triggering circuit including transistor 331, biasing resistors 333 and 335, diode 337 and an RC network including capacitor 339 and resistor 341 connected between the collector of transistor 331 and ground. Also included are comparator 343 driven by the aforementioned positive and negative 15-volt power supplies through voltage limiting zener diodes 305 and 307, a second transistorized triggering circuit including transistor 345, biasing resistors 347, 349 and 351 and diode 353 which triggering circuit is also connected to the 5-volt supply and a second RC network identical to the previously referred to RC network and including capacitor 355 and resistor 357 and 359. The circuit further includes filter capacitors 361, 363, 365 and 367.

In operation, every pulse provided at the output of the width and peak detector circuit 45 is applied via lead 369 through a current limiting resistor 371 and diode 337 to the base terminal of transistor 331 for triggering the transistor into its conductive state. This, in turn, allows capacitor 339 to charge to the 5-volt level and thereafter discharge through resistor 341. Accordingly, the voltage appearing at junction A connected between the capacitor and resistor and also one input of comparator 343 is an inverse function of the time that has elapsed since the last dark spot signal was coupled to the base of transistor 331. It should be noted that the HLEAD signal provided by the signal timing circuit 39 is also applied to comparator 343. In this manner, during the period in which HLEAD is low, that is, during the period when the electronic video assembly is detecting, the comparator is inhibited from going low. However, during the HLEAD time, that is, when the scan is outside of the window region, the comparator output will be low as along as the voltage at junction B is lower than the voltage at junction A, junction B being connected to the second mentioned RC network and the otherwise free input of comparator 343. Thus, the comparator 343 is triggered into its low state at the beginning of the HLEAD time and remains in that state so long as the voltage at point A is greater than the voltage at point B. During this time the transistor 345 which is connected to the output of comparator 343 through diode 353 and a current limiting resistor 371 is maintained in its conductive state so that the capacitor 355 begins to charge to the 5-volt level. As the capacitor 355 charges, the voltage at point B increases, while the voltage at point A decreases due to the discharge of the capacitor 339. At a certain point during this process the voltage junctions A and B will become equal which in turn will return the comparator 343 to its initial high level state and thereby turn off transistor 345 so that the capacitor 355 begins to discharge. Accordingly, during the HLEAD time the voltage at point A is transferred to point B since, as mentioned above, the voltage at point A is a function of the time which has elapsed since the last dark spot pulse occurred. Further, since this last pulse was the last pulse appearing on the previous horizontal scan line and therefore classified as an edge 2 representative pulse, the voltage at junction B is a function of the time which has elapsed since the bottle's trailing edge was detected on a particular horizontal scan line. The comparator 373 generates an E2 signal which comparator is driven by the positive and negative 15-volt DC supplies referred to hereinabove. This comparator has one input connected to point B while the other input is connected to potentiometer 375, this input being connected to ground through a filter capacitor 377. The comparator compares the voltage at point B with the adjustable voltage appearing across the potentiometer 375. When the voltage at point B decreases due to the discharging of capacitor 355 to a point less than that of the constant voltage across the potentiometer 375, the comparator output goes low so as to produce the E2 signal. This signal which is maintained for a predetermined period of time is applied through lead 379 to the otherwise free input of NAND gate 283 in order to inhibit the NAND gate. It should be readily apparent from the above description, that the time in which comparator 373 goes low to produce the E2 signal is dependent upon the voltage tapped off the adjustable potentiometer 375. This voltage is set so that the E2 signal is initiated slightly before the appearance of the dark spot pulse representing the trailing edge of the bottle being detected. In this way gate 283 is inhibited from responding to this dark spot pulse. This operation repeats itself during each horizontal scan of camera 25, that is, each trailing edge 2 pulse on a given horizontal scan line triggers the aforementioned memory circuit for initiating the E2 signal during the following horizontal scan line so as to thereby suppress the dark spot pulse appearing on that scan line.

It should be readily apparent from the above description that NAND gate 283 is inhibited from producing any pulses for a predetermined period during and after the appearance of the first dark spot pulse, i.e., the leading edge, and for a period before, during and after the appearance of the last dark spot pulse, i.e., the trailing edge, on a given horizontal scan line. Accordingly, any pulse which appears at the output of gate 283 is caused by noise, dirt or some defect in the detected bottle such as, for example, a birdswing, and accordingly, pulses generated at the output of NAND gate 283 are designated bird candidate pulses. In the event that round window timing is being utilized, the NAND operation of NAND gate 283 will not be necessary since there will be no leading or trailing edge signals to be eliminated from consideration. Accordingly, the ANOM output of the width and peak detector 45 is inverted by NAND gate 281 and the signal is then coupled directly to output line 287 via switch 288 which will be closed.

Figure 10:
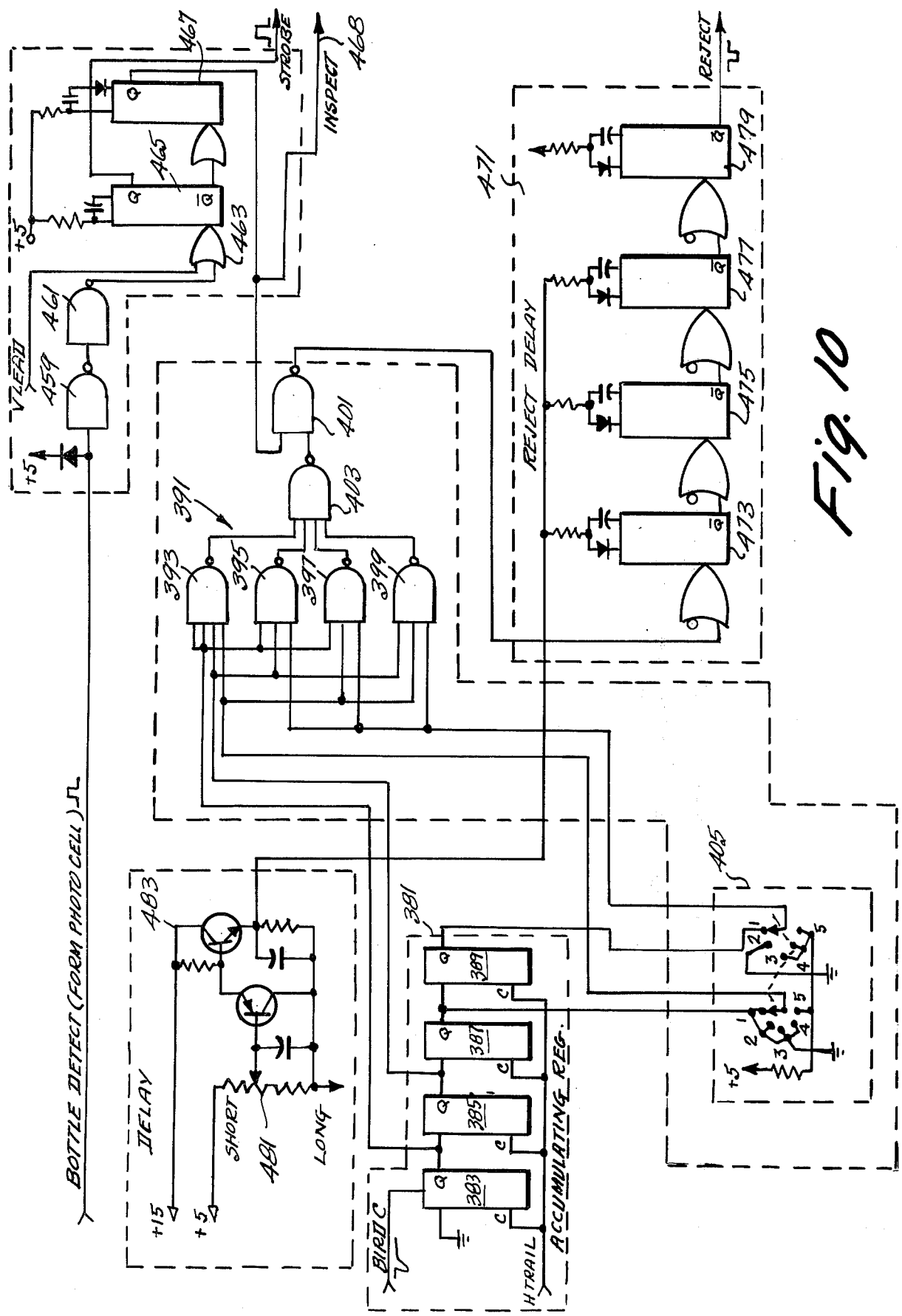
FIG. 10 is a detailed schematic diagram of the logic circuits used in the preferred embodiment of the present invention.

Refer now to FIG. 10 which is a schematic diagram of the logic circuit 57 of the present invention. As briefly stated hereinbefore, this circuit is provided for applying a reject signal to the reject gate activator circuit 65 in the event certain requirements are met. As will be seen hereinbelow, these requirements take into account certain conditions which exist during a given period of detection, i.e., one scan frame. As an example, one of the requirements necessary for producing the aforesaid reject signal at the output of the logic circuit illustrated in FIG. 10 is that during the given or current period of detection, the bottle being detected includes a defect such that the bird candidate pulse provided at the output of the edge removal circuit illustrated in FIG. 9 appears on at least three of four consecutive horizontal scan lines. By providing that a defect pulse must appear on three of four consecutive horizontal scan lines, defect detectivity is maximized while noise susceptibility is minimized. The circuitry necessary for determining whether such a condition has been met includes a shift register generally designated by the numeral 381 which includes four interconnected flip-flop stages 383, 385, 387 and 389, a group of logic NAND gates 391 which include a four input NAND gate 393, and three input NAND gates 395, 397 and 399 together with NAND gate 403 and an inhibit gate 401. Operationally, each of the birdswing candidate signals, i.e., defect pulses, produced during the period of detection is applied to the first flip-flop 383 of shift register 381 which sets the flip-flop stage for producing a high output signal pulse. This high output pulse is applied to one input of each of the three NAND gates 393, 395 and 397. The HTRAIL signal derived from the timing circuit 34 is applied to the clock input of the various flip-flop stages. In this manner during the HTRAIL time, that is the time period in a horizontal line scan after the window portion thereof, the contents of the various flip-flops are shifted forward. Accordingly, the high output signal produced at flip-flop stage 383 during a given horizontal scan line is shifted to the second flip-flop stage 385 at the end of that scan line and so on. As illustrated, the output of the next flip-flop stage 385 is connected to an input of each of the NAND gates 393, 395 and 399. The output of flip-flop stage 387 is applied to an input of each of the NAND gates 393, 397 and 399 while the output of the last flip-flop stage 389 is applied to the inputs of NAND gates 395, 397 and 399. It should be readily apparent that if three defect pulses are produced during any four consecutive horizontal scan lines, one of the four NAND gates 393, 395, 397 and 399 will go low at its output and since the output of these NAND gates is connected to the inputs of NAND gate 403, this NAND gate will go high. This situation is classified as a detected defect.

A switching arrangement 405 is provided wherein the requirements for classifying a detected defect can be modified from the aforementioned three bird candidate signals detected in a four horizontal line scan interval to a number of other defect detect decision criteria by means of switch 405. Thus, when the switch is closed in the first switching position illustrated in FIG. 10, three horizontal scan lines must provide a bird candidate defect signal in a four horizontal line scan interval in order to provide a defect detected signal at the output of gate 403. When switched to the next succeeding position, i.e., position 2, bird candidate defect pulses must appear on three consecutive horizontal scan line intervals in order to generate a defect pulse at the output of NAND gate 403. In switch position three, two consecutive bird candidate defect signals must be detected in a two horizontal line scan interval. When the switch 405 is in position four, two bird candidate defect pulses must occur in a three horizontal line scan interval, and with the switch in position five, a defect pulse will be generated if a single bird candidate defect signal is generated in a given horizontal line scan.

Another condition must be met during the given period of detection, namely, that a bottle in fact is being detected. While this may appear self-evident and unnecessary in view of the foregoing, it should be realized that the logic circuit responsive to the defect or bird candidate pulses will not always indicate the presence of a bottle, i.e., when there is no defect in the bottle being detected, a defect pulse will not be generated and therefore will not indicate the presence of a bottle. Accordingly, logic circuitry required to determine the presence of a bottle is necessary and accordingly reference is made to the bottle detect circuitry 59 illustrated in FIG. 11.

Figure 11:
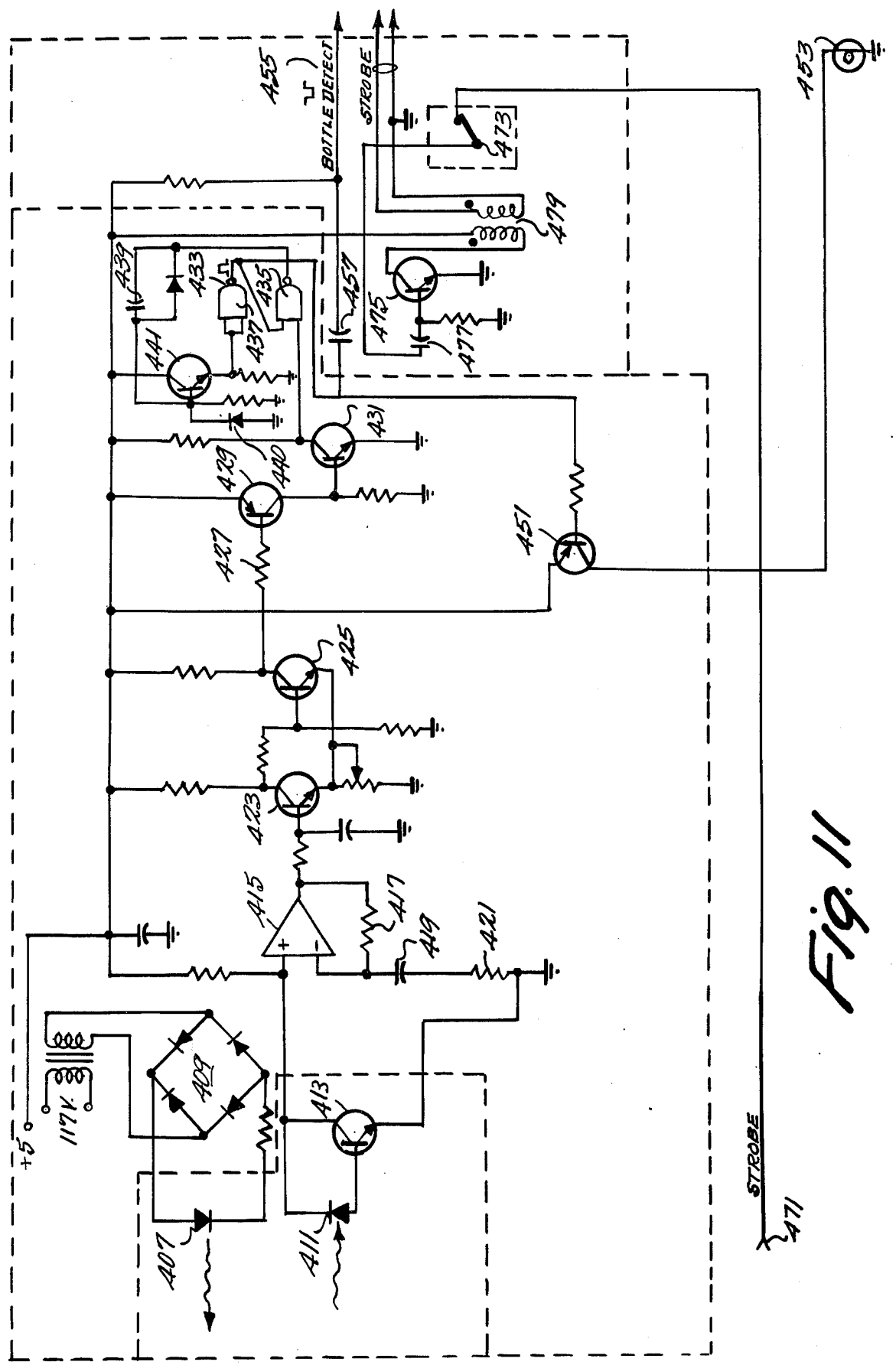
FIG. 11 is a detailed schematic diagram of the bottle detector and strobe trigger circuit of the preferred embodiment of the present invention.

Referring to FIG. 11 there is disclosed a light emitting diode 407 which is powered from a typical 117 volt AC source which is full/wave rectified by a bridge rectifier circuit 409 of conventional design. The light generated by the light emitting diode 407 is received by a photocell 411 of conventional design. Photocell 411 is connected across the collector-base junction of transistor 413, which transistor is turned on when photocell 411 receives light and is turned off when no light impinges upon the photocell. The light beam from light emitting diode 407 is reflected from a bottle to be inspected when the bottle passes in front of the diode. This reflected light is directed back to photocell 411. Accordingly, when a bottle to be inspected passes in front of the light emitting diode 407, the reflected light beam decreases the resistance of diode 411 thereby turning transistor 413 on. With transistor 413 turned on, a negative going signal is coupled to the non-inverting input of an operational amplifier 415. The operational amplifier 415 includes a feedback resistor 417 and a filtering arrangement including capacitors 419 and 421. The filter capacitor 419 is required to prevent the noise generated by the bridge rectifier circuit from affecting the operation of the bottle detection circuit. The amplifier 415 provides a low output in response to the negative going input signal, which output is coupled to a Schmitt trigger circuit which includes transistor 423 and 425. The low input signal to the base of transistor 425 turns this transistor off, thereby driving the voltage at the base of transistor 425 in the positive direction. Accordingly, transistor 425 turns on. The output of transistor 425 therefore goes low, with this low signal being coupled to transistor 429 via current limiting resistor 427. In response, transistor 429 is turned on, thereby driving the voltage at the base of transistor 431 in the positive direction. Transistor 431 is accordingly turned on, thereby driving its output low. This low output is coupled to a monostable circuit 433 which includes a flip-flop circuit formed of NAND gates 435 and 437, a feedback capacitor 439 and a transistor 447. Initially, the output of NAND gate 435 is low, with this low signal being applied to the base of transistor 447 via capacitor 439. Hence, transistor 447 is in an off state, thereby providing a low signal to the input terminals of NAND gate 437. Thus, the output of NAND gate 437 is normally high. When, however, transistor 431 provides a low signal at its output indicating the presence of a bottle to be inspected, the low signal causes NAND gate 435 to provide a high signal at its output. This high signal is coupled to the base terminal of transistor 447 via capacitor 439. Hence, transistor 447 turns on, thereby providing a high signal to the input terminals of NAND gate 437. Thus the output of NAND gate 437 goes low to thereby provide at output terminal 455 a low signal via coupling capacitor 457. In addition, this low signal is coupled to transistor 451 causing transistor 451 to turn on, thereby energizing a bottle detect lamp 453 to visually indicate the presence of a bottle being inspected. After a predetermined time, as established by the value of capacitor 439 and resistor 440, the transistor 447 is again turned off, thereby returning the output of NAND gate 437 to the high state. This high signal is coupled to the base of transistor 451 to turn this transistor off, thereby deenergizing lamp 453 and at the same time is coupled to the output terminal 455 of the bottle detection circuit via capacitor 457.

Return now to FIG. 10 for discussion of the strobe fire and reject inhibit logic. The output of the bottle detect circuit is coupled to a double inverting amplifier which includes NAND gate 459 and NAND gate 461, which gates provide a slight delay in the low bottle detect signal generated by the monostable circuit 433 of FIG. 11. This signal is coupled via the NAND gates 459 and 461 to a monostable circuit 465. In response thereto, the monostable circuit provides a positive going output at its Q terminal and a low output at its $\overline{Q}$ output. The positive going output of the monostable circuit 465 is coupled to the strobe fire circuitry illustrated in FIG. 11.

Accordingly, refer now back to FIG. 11. The positive or high strobe fire signal is coupled to input terminal 471 and is coupled directly via a switch 473 to the base terminal of transistor 475 via a capacitor 477. Transistor 475 is thereby turned on so that current from the 5-volt supply is coupled to the primary windings of transformer 479. The 5-volt source supply is transformed and coupled to a gating SCR in the strobe light circuit 21 shown in FIG. 3 to thereby couple a 2.5 volt AC strobe light energizing voltage across the strobe light.

Return now back to FIG. 10. The monostable circuit 465 is set to remain in its metastable state for a time sufficient to permit the electrical noise generated by the strobe lamp to die down. After the monostable circuit 465 has returned to its stable state, a high output is generated at the $\overline{Q}$ output thereof which signal is coupled to a second monostable circuit 467 which in response thereto provides a positive going output at its Q output. This positive output is coupled via output terminal 468 to the clipping circuit input terminal 273 illustrated in FIG. 8 to enable a clipping operation. The positive going or high output signal is also coupled to NAND gate 401 for enabling NAND gate 401 to provide a high output when NAND gate 403 provides a low output. It will be remembered that NAND gate 403 provides a low output whenever anyone of the NAND gates 393, 395, 397 and 399 provides a low output in response to the satisfying of defect detect conditions set forth hereinabove. Accordingly, the defect signal classification circuitry 391 is synchronized with the strobe mechanism so that a reject signal is produced at the output of NAND gate 401 only if a defect is actually classified and a strobe signal has been fired. The output of the NAND gate 401 is coupled to a reject delay circuit 471 which includes a series of monostable multivibrator circuits 473, 475, 477 and 479. Upon receipt of the reject signal at the output of NAND gate 401, multivibrator 473 is driven into its metastable state and remains there for a predetermined period of time. After the timing out of multivibrator 473, multivibrator 475 goes into its metastable state for a predetermined period of time. This continues down the line until multivibrator 477 times out, whereupon the output signal from multivibrator drives the $\overline{Q}$ output of multivibrator 479 positive. This signal is provided for initiating a bottle reject means such as disclosed in FIG. 12, thereby removing the defective bottle from the conveyor mechanism 11.

It should be readily apparent that the overall time required for all of the multivibrators to time out is the same as the time required for the defective bottle to reach the reject gate. In this regard it should be noted that the timing periods for the multivibrators can be adjusted by a potentiometer 481 and an associated direct current amplifier circuit 483. Thus, when the center tap of the potentiometer is moved toward the terminal of the potentiometer 481 connected to a 5-volt supply, the reject delay period is reduced whereas when the center tap is moved toward the ground terminal of the potentiometer the reject delay period is increased.

Figure 12:
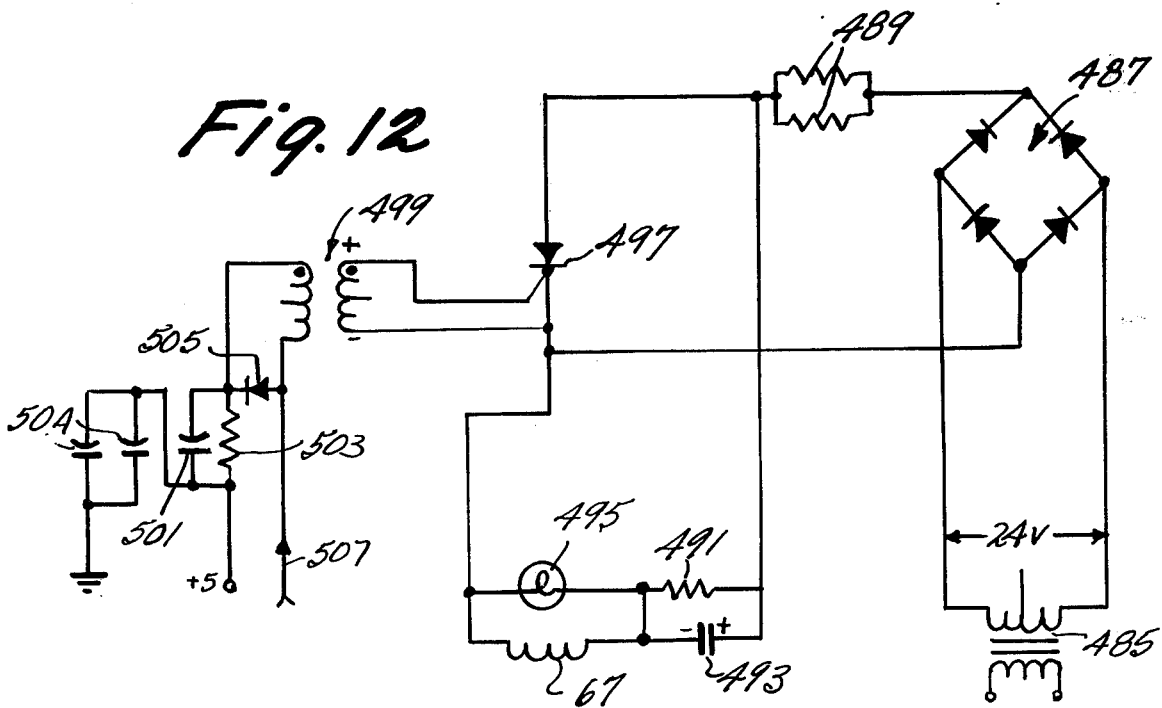
FIG. 12 is a detailed schematic illustration of the reject driver utilized in the preferred embodiment of the present invention.

Turn now to FIG. 12 which is a schematic illustration of the reject gate drive circuit of the present invention. A transformer 485 of conventional design transforms an 120 volt line voltage down to 24 volts. This voltage is full waved electrified by a bridge rectifier 487. The output of the bridge rectifier 487 is connected to the relay coil 67 of the reject gate drive mechanism via high wattage, limiting resistors 489, resistor 491 and capacitor 493. A reject lamp 495 is illustrated which is energized whenever the reject gate is actuated. An SCR 497 is connected across the output terminals of the bridge rectifier 487 and across solenoid 67 and the parallel combination of capacitor 493 and resistor 491. The SCR 497 has its gate terminal connected to the secondary of a transformer 499. A 5-volt supply is connected to one end of the primary of the transformer 499 via a parallel arrangement of a capacitor 501 and a resistor 503. The other end of the primary winding is coupled via terminal 507 to the $\overline{Q}$ output of the multivibrator 479 of the reject delay circuit illustrated in FIG. 10. Capacitor 501 provides filtering so that noise voltages do not turn on the SCR 497. The diode 505 limits voltage spikes in the primary of the transformer 499.

Capacitor 493 in FIG. 12 is charged through current limiting resistors 489. The reject solenoid 67 provides a ground reference for capacitor 493 to charge to the voltage determined by transformer 485 and diode rectifier bridge 487. In the normal state of operation the capacitor 492 is charged positively and no current is flowing through the solenoid. When a reject signal occurs, terminal 507 of transformer 499 is pulled to ground potential and current flows in the primary causing the secondary to emit a pulse which triggers SCR 497. This SCR discharges capacitor 493 through reject solenoid 67 thus actuating the reject solenoid to reject the inferior ware. Resistor 491 limits the current through lamp 495 during this actuation period. The ringing caused by the solenoid's windings and moving core reverses the current across SCR 497 thus shutting off SCR 497 and releasing the solenoid to return to its off position.

Although a preferred embodiment of the present invention has been illustrated and described, it should be understood that various changes and modifications can be made by those skilled in the art without departing from the spirit and scope of the invention as defined by the following claims.

What is claimed is:

1. An apparatus for video inspection of articles of manufacture comprising:
    a light source for providing light rays to illuminate a sample article,
    a video camera means for scanning said illuminated sample and for producing for each scan line a video signal corresponding to the difference in refraction characteristics of the portion of the sample scanned, and
    means connected to said camera for processing the output signal thereof to produce a defect output signal in response to a scanned defect in said sample, said processing means including
        means for suppressing a predetermined portion of the video signal received from said camera means during each of said scan lines, and
        means for continuously discriminating between the video signals corresponding to desired changes in the refraction characteristics of said sample as said camera scans across said sample and the refraction characteristic produced by defects in said sample.

2. The inspection apparatus of claim 1 wherein said discriminating means comprises a delay line filter means for eliminating the portions of the video output signal corresponding to a differential refractive change having a duration greater than a preselected time period.

3. The inspection apparatus of claim 1 wherein said discriminating means comprises means for normalizing the instantaneous video output signal with respect to the running average of the video signal over a predetermined period of time.

4. The inspection apparatus of claim 3 wherein said suppressing means includes means for shaping the portion of the video signal not suppressed to a circle.

5. The inspection apparatus of claim 3 wherein said suppressing means comprises means for shaping the portions of the video signal suppressed to conform to the outline of the sample article.

6. The inspection apparatus of claim 3 wherein said normalizing means includes means for continuously deriving the average value of said video output signal over a predetermined time period, and means for comparing the instantaneous video signal with said average video signal to thereby normalize said instantaneous video signal with respect to the average of said video signal over a predetermined time period.

7. The inspection apparatus of claim 6 wherein said discriminating means further comprises means for eliminating the portions of said video output signal corresponding to a differential refractive change having a time duration less than a predetermined time interval.

8. The inspection apparatus of claim 7 wherein said eliminating means includes means for generating a voltage having an amplitude which is proportional to the time duration of a video signal corresponding to a change in the refraction of said sample, and means for comparing said voltage with a reference voltage corresponding to said predetermined time interval, said comparing means providing an output corresponding to a defect in said sample when said generated voltage exceeds said reference voltage.

9. An apparatus for the video inspection of glassware wherein said glassware includes desirable non-uniformities therein including lettering, mold marks and/or coloration which vary the intensity and direction of light passing therethrough, comprising:
    a light source for providing light rays to illuminate a sample glassware,
    a video camera means for scanning said illuminated sample and for producing for each scan line a video signal corresponding to the changes in the intensity of the light detected by said camera, and
    means connected to said camera for processing the output signal thereof to produce a defect output signal in response to a scanned defect in said sample, said processing means including
        means for suppressing a predetermined portion of the video signal received from said camera means during each of said scan lines, and
        means for continuously discriminating between the video signals corresponding to said desirable non-uniformities and the video signals produced by defects in said sample.

10. The inspection apparatus of claim 9 wherein said discriminating means includes a delay line filter means for eliminating the portions of the video output signal corresponding to a change in intensity of the light directed from said sample to said camera having a duration greater than a preselected time interval.

11. The inspection apparatus of claim 9 wherein said discriminating means comprises means for normalizing the instantaneous video output signal with respect to the running average of the video signal over a predetermined time interval.

12. The inspection apparatus of claim 11 wherein said suppressing means comprises means for shaping a portion of the video signal suppressed to conform to the outline of the sample article.

13. The inspection apparatus of claim 11 wherein said suppressing means includes means for generating in a video frame a non-suppressed scanning interval which defines a circle, and means for varying the diameter of said circle to correspond to the bottom of a round bottle.

14. The apparatus of claim 11 wherein the horizontal scan of said video camera is directed along the vertical edges of the glassware being inspected to thereby eliminate the changes in intensity of the light detected by said camera generated by the vertical edges of said glassware from the video signal being processed.

15. The inspection apparatus of claim 11 wherein said normalizing means includes means for continuously deriving the average value of said video output signal over a predetermined time period, and means for comparing the instantaneous video signal with said average video signal to thereby normalize said instantaneous video signal with respect to the average of said video signal over a predetermined time period.

16. The inspection apparatus of claim 15 wherein said discriminating means further includes means for eliminating the portion of said video output signal corresponding to a change in the light intensity directed to said camera from said sample having a time duration less than a predetermined time period.

17. The inspection apparatus of claim 16 wherein said eliminating means includes means for generating a voltage having an amplitude which is proportional to the time duration of a video signal corresponding to a change in the intensity of a light directed to said camera from said sample, and means for comparing said voltage with a reference voltage corresponding to said predetermined time period, said comparing means providing an output corresponding to a defect in said sample when said generated voltage exceeds said reference voltage.

18. The inspection apparatus of claim 16 wherein said processing means further comprises means for detecting when a bottle is being inspected, logic means for generating a reject signal when a predetermined number of defect signals have been detected in a predetermined number of horizontal scan intervals of said camera, and means responsive to said reject signal for rejecting the sample being inspected.

* * * * *

UNITED STATES PATENT AND TRADEMARK OFFICE
CERTIFICATE OF CORRECTION

PATENT NO. : 4,002,823
DATED : January 11, 1977
INVENTOR(S) : Van Oosterhout, Jack T.

It is certified that error appears in the above-identified patent and that said Letters Patent are hereby corrected as shown below:

Column 2, line 10, delete "cathoderay" and substitute therefor --cathode ray--.

Column 4, line 53, delete "therefraction" and substitute therefor --the refraction--.

Column 5, line 64, delete "cmaera" and substitute therefor --camera--.

Column 7, line 7, after "section" insert --,--.

Column 7, line 37, delete "sammples" and substitute therefor --samples--.

Column 8, line 19, delete "An" and substitute therefor --As--.

Column 9, line 51, delete "curreent" and substitute therefor --current--.

UNITED STATES PATENT AND TRADEMARK OFFICE
CERTIFICATE OF CORRECTION

PATENT NO. : 4,002,823

DATED : January 11, 1977

INVENTOR(S) : Van Oosterhout, Jack T.

It is certified that error appears in the above—identified patent and that said Letters Patent is hereby corrected as shown below:

Column 10, line 20, invert "$\overline{\text{VTRAIL}}$" and "VTRAIL".

Column 10, line 34, delete "sychronization" and substitute therefor --synchronization--.

Column 10, line 47, delete "the" second occurrence

Column 10, line 48, delete "appropirately" and substitute therefor --appropriately--.

Column 10, line 59, delete "cameral" and substitute therefor --camera--.

Column 12, line 12, delete "11o" and substitute therefor --110--.

Column 13, line 30, delete "symetry" and substitute therefor --symmetry--.

Column 13, line 32, delete "networds" and substitute therefor --networks--.

UNITED STATES PATENT AND TRADEMARK OFFICE
CERTIFICATE OF CORRECTION

PATENT NO. : 4,002,823
DATED : January 11, 1977
INVENTOR(S) : Van Oosterhout, Jack T.

It is certified that error appears in the above—identified patent and that said Letters Patent is hereby corrected as shown below:

Column 15, line 57, delete "209" and substitute therefor --219--.

Column 15, line 66, delete "caparator" and substitute therefor --comparator--.

Column 16, line 56, delete "299" and substitute therefor --229--.

Column 19, line 56, delete "resistor" and substitute therefor --resistors--.

Column 23, line 2, delete "425" and substitute therefor --423--.

UNITED STATES PATENT AND TRADEMARK OFFICE
CERTIFICATE OF CORRECTION

PATENT NO. : 4,002,823

DATED : January 11, 1977

INVENTOR(S) : Van Oosterhout, Jack T.

It is certified that error appears in the above—identified patent and that said Letters Patent is hereby corrected as shown below:

Column 24, line 12, delete "anyone" and substitute therefor --any one--.

Column 24, line 51, delete "an" and substitute therefor --a--.

*Signed and Sealed this*

*Twenty-ninth* Day of *July 1980*

[SEAL]

*Attest:*

*Attesting Officer*

SIDNEY A. DIAMOND

*Commissioner of Patents and Trademarks*